United States Patent
Gallo et al.

(10) Patent No.: US 9,303,258 B2
(45) Date of Patent: Apr. 5, 2016

(54) METHOD AND COMPOSITIONS COMPRISING SMALL RNA AGONIST AND ANTAGONISTS TO MODULATE INFLAMMATION

(75) Inventors: Richard L. Gallo, San Diego, CA (US); Jamie Bernard, Westfield, NJ (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 14/007,823

(22) PCT Filed: Apr. 5, 2012

(86) PCT No.: PCT/US2012/032304
§ 371 (c)(1),
(2), (4) Date: Sep. 26, 2013

(87) PCT Pub. No.: WO2012/138846
PCT Pub. Date: Oct. 11, 2012

(65) Prior Publication Data
US 2014/0031413 A1    Jan. 30, 2014

Related U.S. Application Data

(60) Provisional application No. 61/472,136, filed on Apr. 5, 2011.

(51) Int. Cl.
*C12N 15/11* (2006.01)
*C12N 15/113* (2010.01)
*A61K 31/7105* (2006.01)
*C12N 15/117* (2010.01)

(52) U.S. Cl.
CPC .......... *C12N 15/113* (2013.01); *A61K 31/7105* (2013.01); *C12N 15/117* (2013.01); *C12N 2310/17* (2013.01); *C12N 2330/00* (2013.01); *C12N 2330/10* (2013.01)

(58) Field of Classification Search
CPC .. C12N 15/113; C12N 2330/10; C12N 15/63; C12N 15/111; A61K 31/7105; A61K 38/00
See application file for complete search history.

(56) References Cited

U.S. PATENT DOCUMENTS

| | | | |
|---|---|---|---|
| 6,692,910 B2 | 2/2004 | Rowe et al. | |
| 2002/0058287 A1 | 5/2002 | Graaf et al. | |
| 2002/0192675 A1* | 12/2002 | Zauderer et al. | 435/6 |
| 2003/0082149 A1* | 5/2003 | Rowe et al. | 424/93.21 |
| 2007/0292866 A1* | 12/2007 | Wang et al. | 435/6 |
| 2009/0093425 A1* | 4/2009 | Dowdy et al. | 514/44 |

FOREIGN PATENT DOCUMENTS

| | | |
|---|---|---|
| EP | 1501931 B1 | 11/2009 |
| WO | WO 2008033432 A2 * | 3/2008 |

OTHER PUBLICATIONS

Baharlou, Simin, International Preliminary Report on Patentability and Written Opinion, PCT/2012/032304, The International Bureau of WIPO, Oct. 8, 2013.

* cited by examiner

*Primary Examiner* — Tracy Vivlemore
*Assistant Examiner* — Kate Poliakova-Georgantas
(74) *Attorney, Agent, or Firm* — Joseph R. Baker, Jr.; Gavrilovich, Dodd & Lindsey LLP

(57) ABSTRACT

The disclosure provides methods and compositions for modulating inflammation.

5 Claims, 24 Drawing Sheets

GAUACUUACCUGGCAGGGGAGAUACCAUGAUCACGAAGGUGGUUUUCCCAGGGCGAGGCUUAUCCAUU
GCACUCCGGAUGUGCUGACCCCUGCGAUUUCCCCAAAUGUGGGAAACUCGACUGCAUAAUUUGUGGUA
GUGGGGGACUGCGUUCGCGCUUUCCCCUG (SEQ ID NO:1).

```
                              SEQUENCE LISTING

<160> NUMBER OF SEQ ID NOS: 7

<210> SEQ ID NO 1
<211> LENGTH: 165
<212> TYPE: RNA
<213> ORGANISM: homo sapiens

<400> SEQUENCE: 1
gauacuuacc uggcagggga gauaccauga ucacgaaggu gguuuuccca gggcgaggcu     60
uauccauugc acuccggaug ugcugacccc ugcgauuucc ccaaaugugg gaaacucgac    120
ugcauaauuu gugguagugg gggacugcgu ucgcgcuuuc cccug                    165

<210> SEQ ID NO 2
<211> LENGTH: 32
<212> TYPE: RNA
<213> ORGANISM: Artificial Sequence
<220> FEATURE:
<223> OTHER INFORMATION: snRNA fragment

<400> SEQUENCE: 2
gggagaacca ugaucacgaa ggugguuuuc cc                                   32

<210> SEQ ID NO 3
<211> LENGTH: 40
<212> TYPE: RNA
<213> ORGANISM: Artificial Sequence
<220> FEATURE:
<223> OTHER INFORMATION: snRNA fragment

<400> SEQUENCE: 3
gggcgaggcu uauccauugc acuccggaug ugcugacccc                           40

<210> SEQ ID NO 4
<211> LENGTH: 26
<212> TYPE: RNA
<213> ORGANISM: Artificial Sequence
<220> FEATURE:
<223> OTHER INFORMATION: snRNA fragment

<400> SEQUENCE: 4 cgauuuccc aaaugggga aacucg                                            26

<210> SEQ ID NO 5
<211> LENGTH: 31
<212> TYPE: RNA
<213> ORGANISM: Artificial Sequence
<220> FEATURE:
<223> OTHER INFORMATION: snRNA fragment

<400> SEQUENCE: 5
uaguccccca cugcguucgc gcuuucccu g                                     31
```

```
<210> SEQ ID NO 6
<211> LENGTH: 164
<212> TYPE: DNA
<213> ORGANISM: Homo sapiens

<400> SEQUENCE: 6
atacttacct ggcaggggag ataccatgat cacgaaggtg gttttcccag ggcgaggctt        60
atccattgca ctccggatgt gctgacccct gcgatttccc caaatgtggg aaactcgact       120
gcataatttg tggtagtggg ggactgcgtt cgcgctttcc cctg                        164

<210> SEQ ID NO 7
<211> LENGTH: 164
<212> TYPE: DNA
<213> ORGANISM: Mus Musculus

<400> SEQUENCE: 7
atacttacct ggcaggggag ataccatgat cacgaaggtg gttttcccag ggcgaggtgt        60
atccattgca tccggatgtg ctgaccactg cgatttcccc aaatgcggga aactcgactg       120
cataatttgt ggtagtgggg gactgcgttt gtgctctccc cttt                        164
```

METHOD AND COMPOSITIONS COMPRISING SMALL RNA AGONIST AND ANTAGONISTS TO MODULATE INFLAMMATION

CROSS REFERENCE TO RELATED APPLICATION

This application is a U.S. National Stage Application filed under 35 U.S.C. §371 and claims priority to International Application No. PCT/US2012/032304, filed Apr. 5, 2012, which claims priority under 35 U.S.C. §119 from Provisional Application Ser. No. 61/472,136, filed Apr. 5, 2011, the disclosure of which is incorporated herein by reference.

STATEMENT REGARDING FEDERALLY SPONSORED RESEARCH

This invention was made with Government support under Grant No. AI083358, awarded by the National Institutes of Health. The Government has certain rights in this invention.

TECHNICAL FIELD

The disclosure relates to agonists and antagonists of inflammation and more particularly to agents that can regulate inflammation in the skin.

BACKGROUND

Humans are susceptible to severe short and long-term damage due to excessive solar exposure. If tissue damage occurs, inflammation is important for both resisting infection and repairing damage.

SUMMARY

The disclosure provides a mechanism by which ultraviolet (UV) light exposure causes inflammation in skin. Further the disclosure provides methods and compositions useful to modulate inflammation and sunburn response.

The disclosure provides a composition comprising isolated photo-fragmented U1 snRNA oligonucleotides.

The disclosure also provides composition comprising isolated fragments of a U1 snRNA wherein the U1 snRNA comprises SEQ ID NO:1, wherein the fragments induce TNF-α and/or IL-6 expression or production in a cell. In another embodiment, the fragments comprise UVB U1 snRNA. In another embodiment, the fragments are selected from the group consisting of (i) a fragment of a loop "a" of U1 snRNA consisting of 10-32 nucleotides of GGGAGAAC-CAUGAUCACGAAGGUGGUUUUCCC (SEQ ID NO:2); (ii) a fragment of a loop "b" of U1 snRNA consisting of 10-40 nucleotides of GGGCGAGGCUUAUCCAUUGCACUC-CGGAUGUGCUGACCCC (SEQ ID NO:3); (iii) a fragment of a loop "c" of U1 snRNA consisting of 10-26 nucleotides of CGAUUUCCCCAAAUGUGGGAAACUCG (SEQ ID NO:4); (iv) a fragment of about 10-100 nucleotides of U1 snRNA (SEQ ID NO:1); (v) any of the foregoing sequences wherein U is T; (vi) complements of any of the foregoing sequences; (vii) any of the foregoing sequences comprising a non-natural nucleotide; and (viii) an oligonucleotide having 90-99% identity with any of the foregoing sequences wherein the oligonucleotide can stimulate IL-6 and/or TNFα production in a mammalian cell. In yet a further embodiment of any of the preceding embodiments, the fragmented oligonucleotides are obtained using UVB exposure of a synthetic U1 snRNA to obtain UVB U1 snRNA. In yet another embodiment, the UVB-U1 snRNA molecules induce TNF-alpha and/or IL-6 expression or production in vivo. In yet a further embodiment, the UVB-U1 snRNA molecules are less than 100 nucleotides in length. In another embodiment, the UVB-U1 snRNA comprise the double stranded regions of loop a, b and/or c of U1 snRNA.

The disclosure also provides a method of identifying an agonist or antagonist of inflammation comprising contacting a cell or tissue comprising U1 snRNA with a potential agonist or antagonist and measuring the production of UVB-U1 snRNA products or TNF-alpha and/or IL-6 expression upon exposure or non-exposure to UV light, wherein an agonist is a compound that promotes UVB-U1 snRNA, TNF-alpha, and/or IL-6 production in a cell or tissue and wherein an antagonist is a compound that inhibits UVB-U1 snRNA production, TNF-alpha, and/or IL-6 production in the cell or tissue when exposed to UV light. In one embodiment, the agonist or antagonist is selected from a protein, polypeptide, oligonucleotide, polynucleotide, and small molecule.

In another embodiment, agonists of U1 snRNA are provided and methods of use thereof. Such compositions include isolated U1 snRNA, modified U1 snRNA and polynucleotides having 90% or greater identity (e.g., 91, 92, 93, 94, 95, 96, 97, 98, or 99% identity to a sequence consisting of SEQ ID NO:1. An agonist of U1 snRNA can be used to treat inflammatory disease and disorders including, but not limited to, psoriasis and itch. For example, the disclosure contemplates administering a U1 snRNA agonist to a subject suffering from psoriasis alone or in combination with a UVB U1 snRNA antagonist. In some embodiments, the method may include phototherapy or other anti-inflammatory therapy. The method includes administering the U1 snRNA agonist topically to a subject at a site to be treated (e.g., a psoriasis or itch site on the skin).

The disclosure also provides a pharmaceutical composition comprising any of the foregoing compositions. In one embodiment, the composition is formulated for application to the skin.

The disclosure also provides a method of inducing inflammation comprising contacting a tissue with a UVB U1 snRNA, wherein the UVB U1 snRNA induces TNF-alpha and/or IL-6 expression or production.

The disclosure also provides a method of treating an infection in a subject comprising contacting a tissue with a composition as set forth above, wherein the composition induces TNF-alpha and/or IL-6 production. In one embodiment, the infection is a skin infection.

The disclosure also provides a method of treating a skin wound or cancer comprising contacting a tissue with a composition as set forth above, wherein the composition induces TNF-alpha and/or IL-6 production.

The disclosure also provides a method of treating an inflammatory disease or disorder comprising contacting a subject with an antagonist of UVB U1 snRNA activity. In one embodiment, the antagonist is an antibody that specifically binds to a TLR3 receptor and inhibits the interaction of the TLR3 receptor with a UVB U1 snRNA. In another embodiment, the antagonist is an antibody that specifically binds to UVB U1 snRNA and inhibits the interaction of the UVB U1 snRNA with a TLR3 receptor. In yet another embodiment, the antagonist is an oligonucleotide siRNA that binds to a UVB U1 snRNA. In yet a further embodiment, the inflammatory disease or disorder is selected from the group consisting of acne, rosacea, atopic dermatitis, contact dermatitis, drug eruptions, psoriasis, seborrheic dermatitis, lupus, scleroderma, rheumatoid arthritis, blistering disease bullous pemphigoid or pemphigus, inflammatory hyperpigmentation, melasma and vitiligo, and urticaria or hives.

The disclosure provides the use of RNA oligonucleotides as adjuvant therapies, and to stimulate the inflammatory response during circumstances of both infection and cancer. Anti RNAs could be synthesized to block the effects of U1 RNA or TLR3 antagonists could be used to reduce solar aging and attenuate inflammation from sunburn or other forms of tissue necrosis such as injury and radiation.

UVB irradiation of keratinocytes altered non-coding RNAs including U1 small nuclear RNA (snRNA), and direct analysis of U1 snRNA demonstrated that when exposed to UVB, U1 snRNA is then recognized by TLR3 and can induce a classical UV inflammatory cascade through nuclear factor-kappaB (NF-kB). Confirmation of this response was seen in vivo since mice exposed to UVB but lacking TLR3 were unable to increase TNF-α or IL-6.

DETAILED DESCRIPTION

Figure 1:
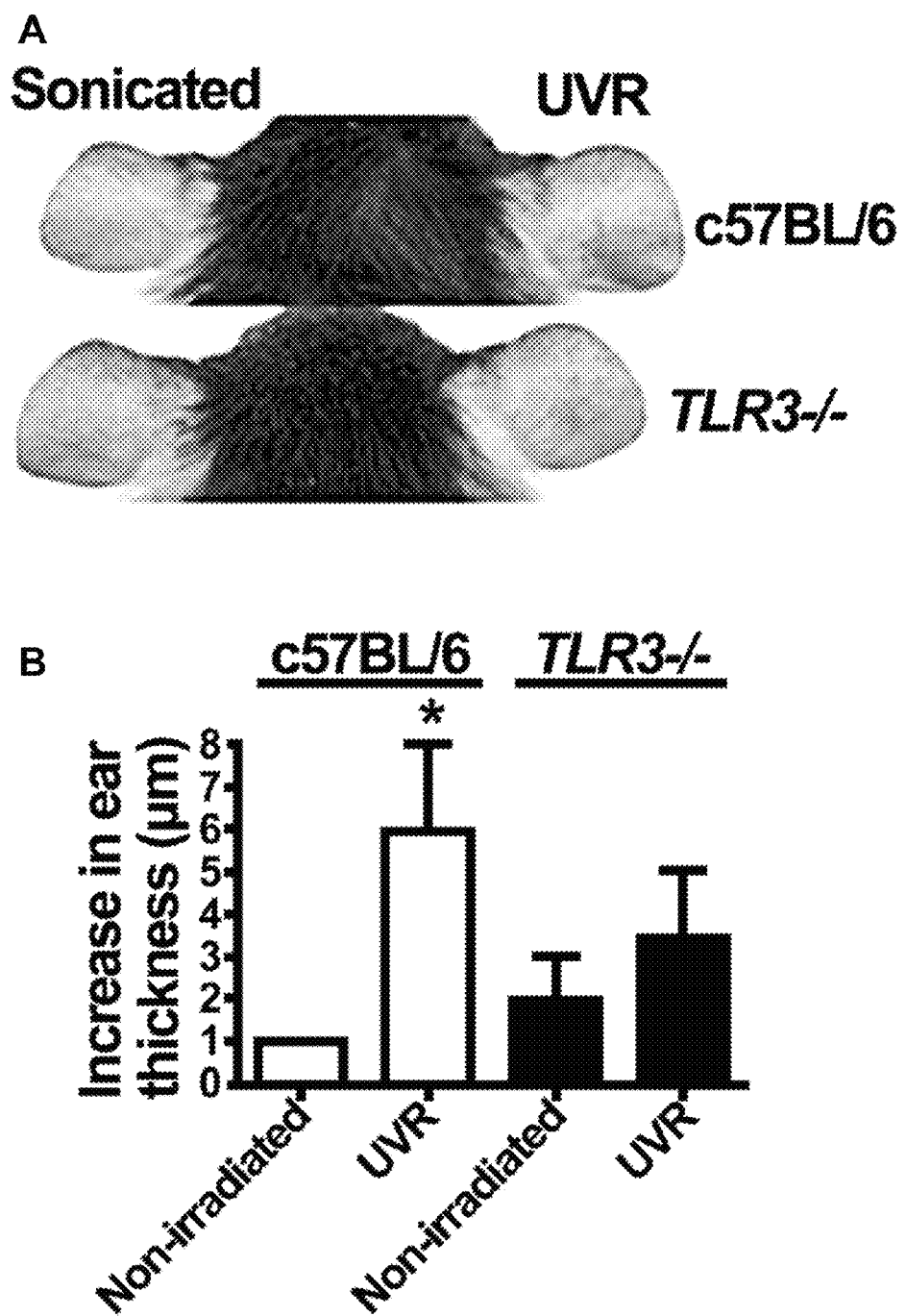
FIG. 1A-J shows RNA generated after UVR-induced keratinocyte necrosis is an inducer of inflammation. (A) Mouse ears 24 hrs following ear injections of normal keratinocyte preparations or keratinocytes after exposure to 15 mJ/cm$^2$ UVB (n=4). (B) Micrometer measurements of ear thickness 24 hrs following ear injections of keratinocytes treated with UVB or unirradiated as control ($*p<0.05$). qRT-PCR analysis of TNF-α (C) ($*p<0.05$) or IL-6 (D) ($*p<0.001$) 24 hrs following ear injections of keratinocytes treated with UVB or unirradiated as control. qRT-PCR analysis of TLR3 (E) ($*p<0.001$) and TNF-α (F) ($***p<0.001$) from keratinocytes expressing TLR3 siRNA constructs after 24 hrs of culture with preparations keratinocytes treated with UVB or unirradiated as control. (G) ELISA analysis of TNF-α and IL-6 from keratinocytes expressing TLR3 siRNA constructs after 24 hrs of culture with preparations of keratinocytes treated with UVB or unirradiated as control. ($*p<0.05$). Keratinocytes treated with UVB or unirradiated as control were treated with an RNAse then added to separate cultures of normal human keratinocytes. After 24 hrs, TNF-α mRNA was measured by qRT-PCR (H) ($***p<0.001$) and TNF-α protein was measured by ELISA (I) ($*p<0.05$). (J) Keratinocytes treated with UVB or unirradiated as control were treated with an RNAse then added to separate cultures of PBMCs. TNF-α protein was measured by ELISA. ($*p<0.05$).
Figure 1:
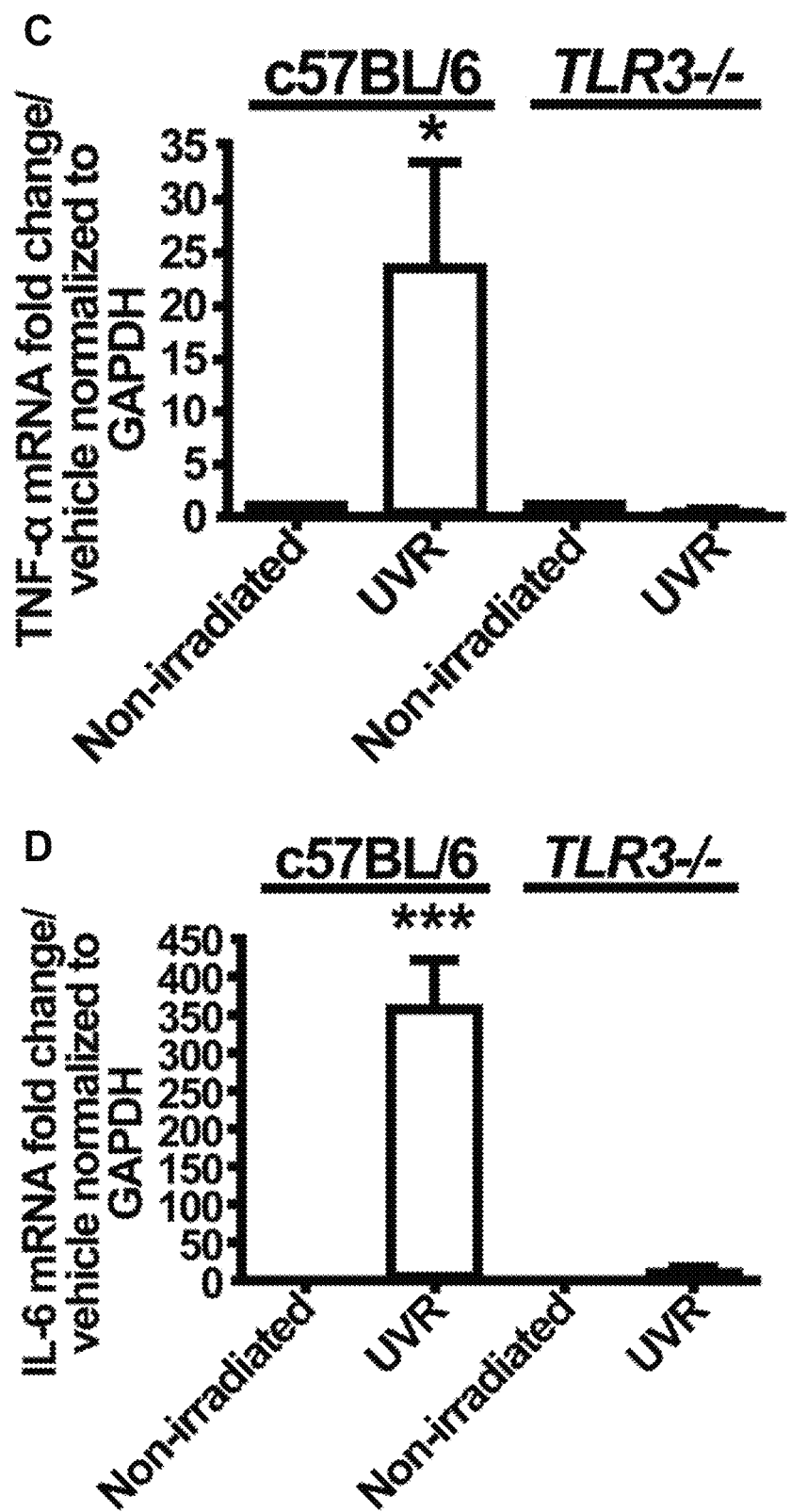
Figure 1:
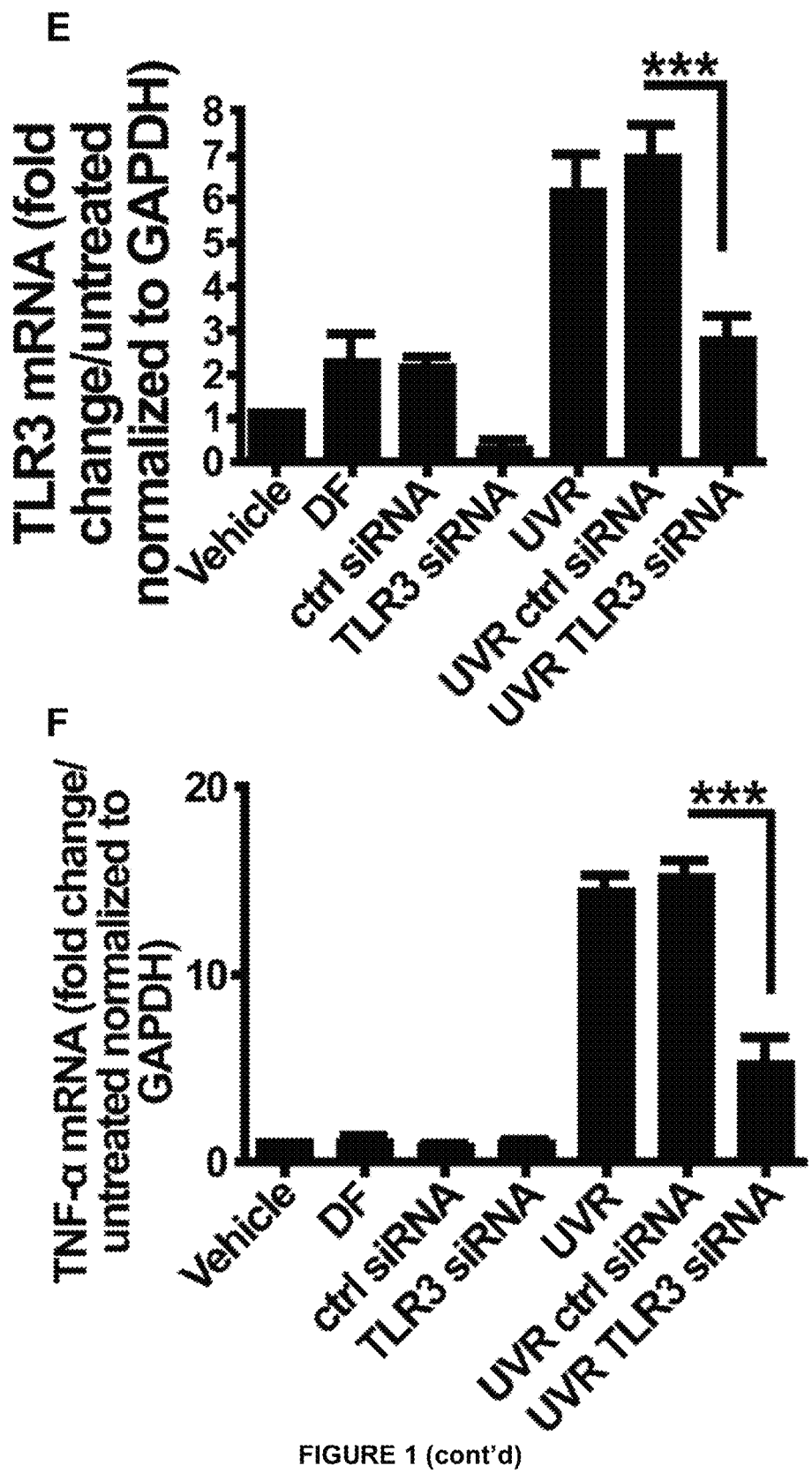
Figure 1:
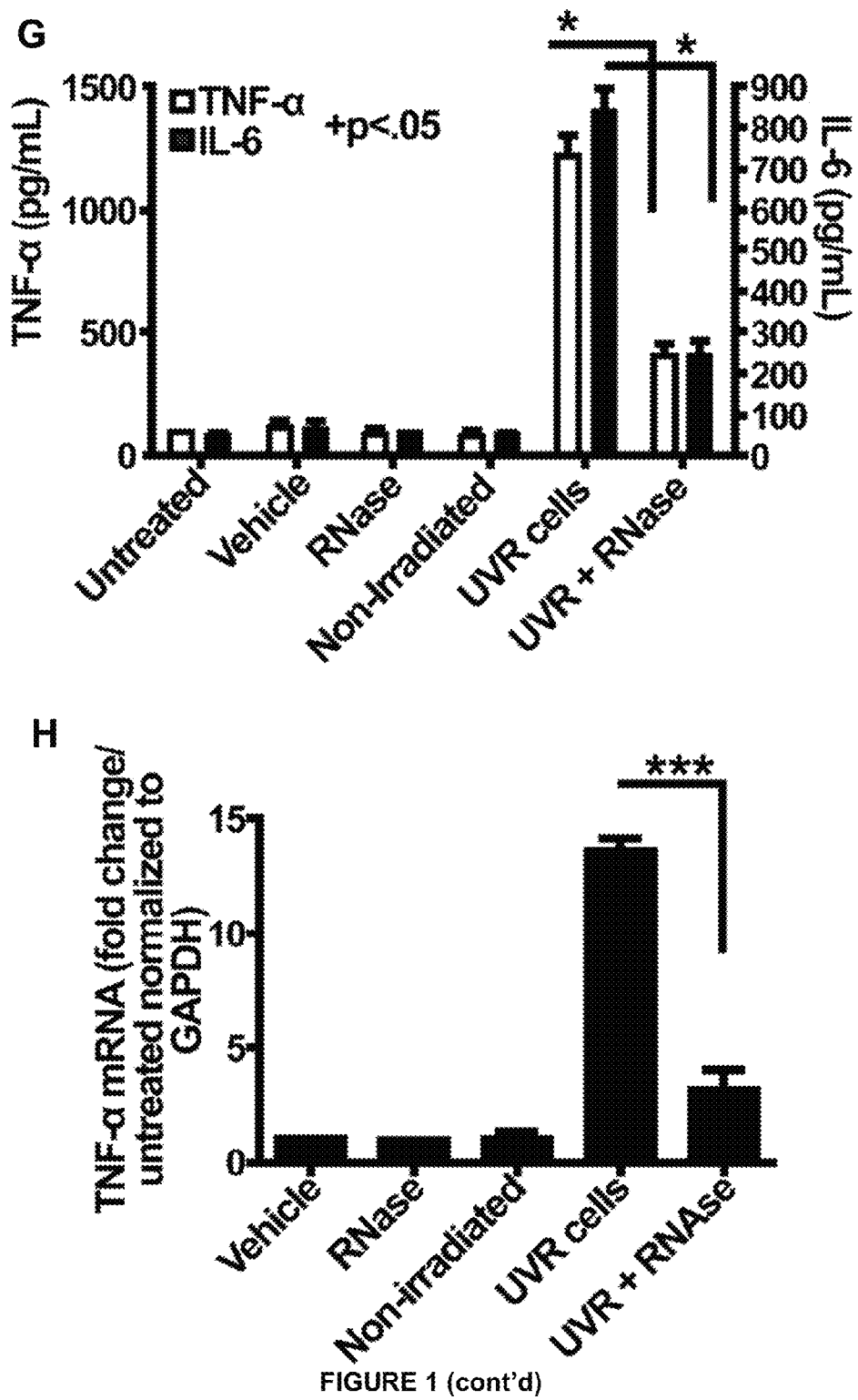
Figure 1:
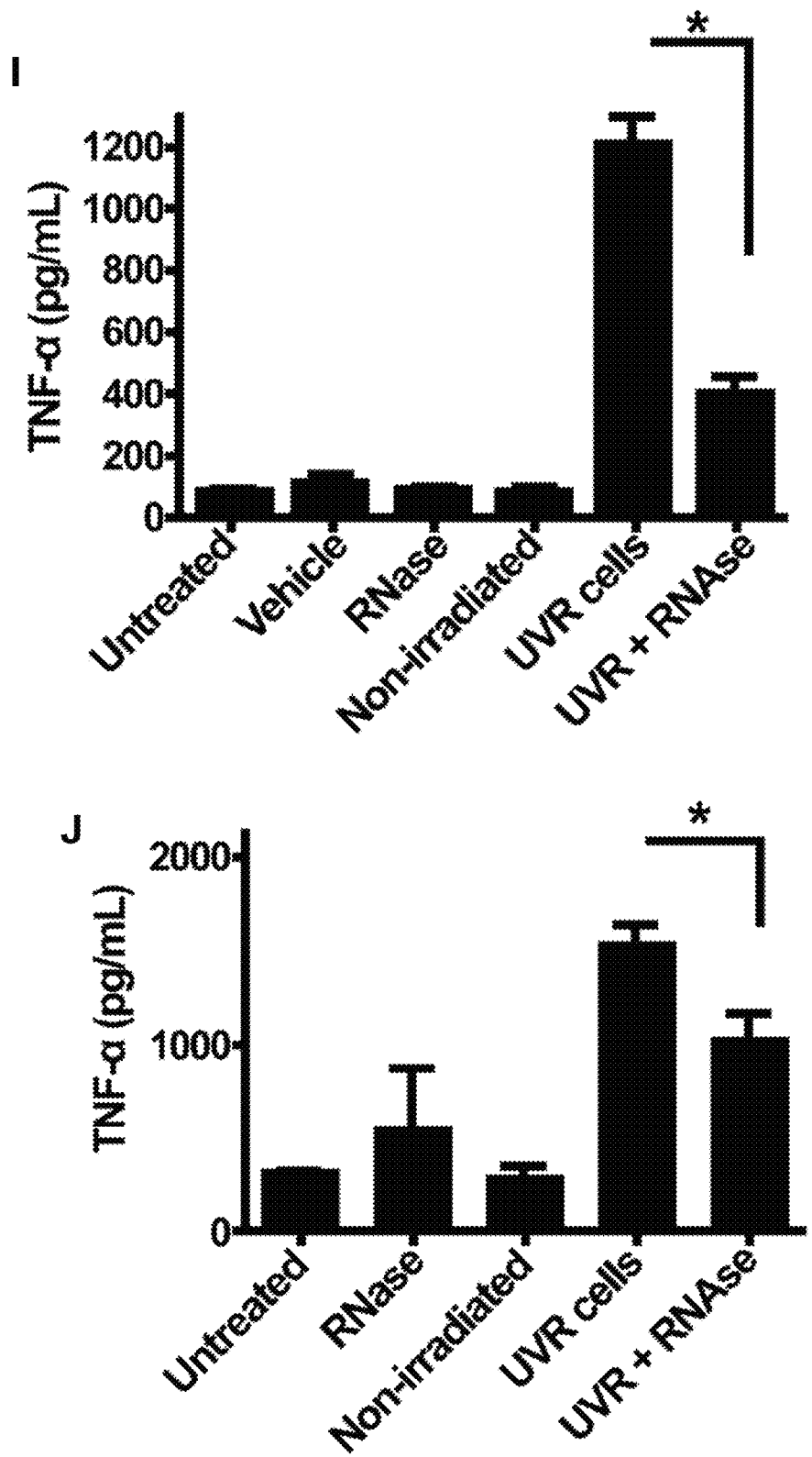

As used herein and in the appended claims, the singular forms "a," "and," and "the" include plural referents unless the context clearly dictates otherwise. Thus, for example, reference to "a compound" includes a plurality of such compounds and reference to "the cell" includes reference to one or more cells known to those skilled in the art, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. However, with respect to any similar or identical terms found in both the incorporated publications or references and those expressly put forth or defined in this application, then those terms definitions or meanings expressly put forth in this application shall control in all respects. The publications discussed above and throughout the text are provided solely for their disclosure prior to the filing date of the present application. Nothing herein is to be construed as an admission that the inventors are not entitled to antedate such disclosure by virtue of prior disclosure.

Excess exposure to ultraviolet (UV) radiation reaching the earth's surface in the ultraviolet B (UVB) wavelength range (280-320 nm) results in an acute inflammatory reaction. This response is essential to trigger repair of injury, induce a protective tanning response, educate the individual to limit further solar exposure, and also contributes to skin cancer development. Despite abundant evidence that sun exposure and a history of sunburn is an important risk factor for developing skin cancer the frequency of sunburn in the general population remains high, with studies indicating most individuals experience sunburn in their lifetime. Thus, despite the need for continued efforts to prevent solar injury, a better understanding of the sunburn response is needed to adequately address this major environmental hazard.

Several chromophores for UV have been well established which include cis-urocanic acid (cis-UCA), DNA, and lipids. While UV only penetrates a few millimeters into the skin, recognition systems need to be in place for these damaged nucleic acids, lipids in proteins to initiate both local and systemic immunological and inflammatory effects. Currently, it is not clearly understood how UV injury is detected, but several downstream elements in the acute sunburn response have been partially described. UV exposure triggers cellular activation of nuclear factor-kappa B (NF-B), which leads to the induction of several cytokines including tumor necrosis factor-alpha (TNF-$\alpha$) and interleukin-6 (IL-6). TNF-$\alpha$ is thought to be important for the response to UV damage as it induces apoptotic signaling, is a potent pro-inflammatory cytokine and may mediate many of the immunomodulatory effects of UV. A critical role for TNF-$\alpha$ in the outcome from UV damage of the skin is supported by observations that anti-TNF-$\alpha$ antibodies reduce the number of sunburn cells generated after UVB exposure and that anti-TNF therapies have been associated with an increased risk of non-melanoma skin cancers. In addition, intradermal injections of TNF-$\alpha$ impair contact hypersensitivity and UV-induced contact hypersensitivity impairment may be reversed with anti-TNF. Therefore, TNF-$\alpha$ is a major pleiotropic inflammatory cytokine whose expression is an essential defense mechanism following solar injury, but the mechanism that initiates the cytokine response is unknown.

The disclosure demonstrates that the cutaneous innate immune system plays an important role in the early inflammatory response to UV and that photodamage to self-non-coding RNA serves as one molecular trigger of injury. Modulating the inflammatory response using U1 RNA and fragments thereof to promote inflammation can be helpful in treating skin infections and cancer. In addition, inhibiting the activity of the U1 RNA and fragments (e.g., by antibodies against U1 RNA or TLR3) can be useful to inhibit skin damage due to UV irradiation.

This disclosure provides methods and compositions that comprise U1 RNA oligonucleotides as adjuvant therapies to stimulate the inflammatory response for diseases that would respond well to inflammation, such as infectious diseases and cancer. Conversely, anti RNAs could be synthesized to block the inflammatory effects of U1 small nuclear RNA (snRNA), or TLR3 antagonists could be used to reduce solar aging and attenuate inflammation from sunburn or other forms of tissue necrosis such as injury and radiation.

Small nuclear ribonucleic acids (snRNAs) are essential components of small nuclear ribonucleoprotein complexes (snRNPs) which, when assembled with additional proteins, form the large ribonucleoprotein complex known as the splicesome. The splicesome is responsible for precursor mRNA splicing; the process that removes introns from RNA transcripts before protein production. An individual snRNA is generally about 250 nucleotides or less in size (Alberts, B. et al., "Molecular Biology of the Cell", Third Edition, Garland Publishing, Inc., New York, 1994, 365-385). The various splicesome snRNAs have been designated as U1, U2, U3 . . . U12, due to the generous amounts of uridylic acid they contain (Mattaj, I. W. et al., 1993, FASEB J 15 7:47-53).

U1-snRNP comprises U1-snRNA (also called the U1-RNA (SEQ ID NO:1)), the seven common core Sm proteins, and three U1-specific proteins (U1-70K, U1-A, and U1-C). The crystal structure of the U1-snRNP complex, together with previous structural and biochemical data, reveals how the molecules of this complex are assembled.

Figure 5A:
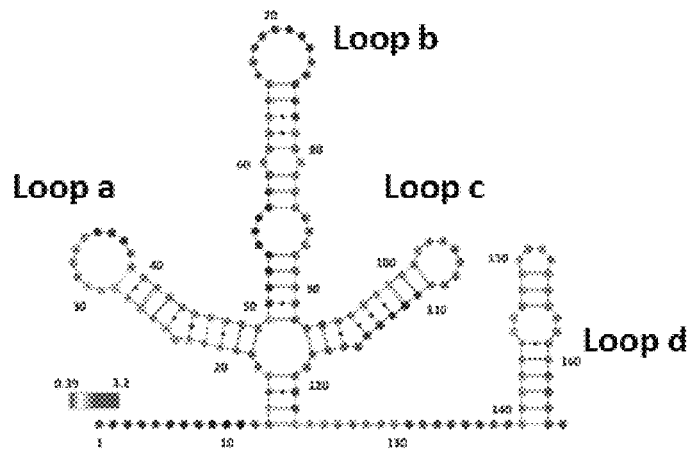
FIG. 5A-B shows a diagram of U1 RNA and sequences (A). (B) Loops are identified in the U1 RNA including loop a, b, c and d (SEQ ID NO:1).

The U1-RNA molecule is 165 nucleotides in length (SEQ ID NO:1) and forms four stem loops that resemble an asymmetrical X-shape (FIG. 5A; SEQ ID NO:1). The seven Sm proteins are bound to the Sm binding site on U1-RNA, which is located between stem loops 3 ("c") and 4 ("d"), forming the particle core. The X-ray crystal structures of heteromeric Sm proteins (D1-D2) and (B-D3) led to an early model where the Sm proteins form a ring around the central RNA molecule. This model was supported by a single particle electron microscopy (EM) structure of the U1-snRNP complex at 10 Å resolution that revealed a 'doughnut' shape composed of Sm proteins in a circular arrangement. The recent crystal structure of U1-snRNP also supports the ring model, with interactions between the RNA backbone and Sm proteins stabilizing the core.

The sunburn response is a common event with significant medical consequences. The disclosure demonstrates that UV-damaged cells release a soluble signal that potently stimulates cytokine production from undamaged keratinocytes and peripheral blood mononuclear cells (PBMCs). The UV-injury signal was found to be damaged self-RNAs that are detected by TLR3. Through transcriptome sequencing of RNAs from UV-exposed cells, alterations in stem-loop domains of non-coding RNAs after UV exposure were identified, and UV damage to U1 RNA was sufficient to directly trigger cytokine production in a TLR3- and TRIF-dependent manner. As predicted by these observations, an increase in TNF-$\alpha$ in the skin following UVB exposure was abrogated in TLR3$^{-/-}$ or TRIF$^{-/-}$ mice. TLR3$^{-/-}$ mice failed to exhibit UV-induced suppression of contact hypersensitivity. Thus, these findings establish for the first time that TLR3 detects UV damage to self-RNA, and that this serves as a critical signal of solar injury.

The disclosure provides U1 snRNA useful in methods and compositions of the disclosure. A U1 snRNA includes (i) a sequence as set forth in SEQ ID NO:1, (ii) a sequence as set forth in SEQ ID NO:1 wherein one or more nucleotides are substituted with a non-natural nucleotide; (iii) a sequence that is 90% or more identical to SEQ ID NO:1 and which has a biological activity of a native U1 snRNA such as, but not limited to, binding Sm proteins, similar crystal structure and the like.

The disclosure provides isolated UVB-U1 snRNA molecules that induce TNF-alpha and/or IL-6 production. In one embodiment, the UVB-U1 snRNA molecules are less than 100 nucleotides in length. In another embodiment, the UVB-U1 snRNA comprise the double stranded regions of loop "a", "b" and/or "c".

Figure 5B:
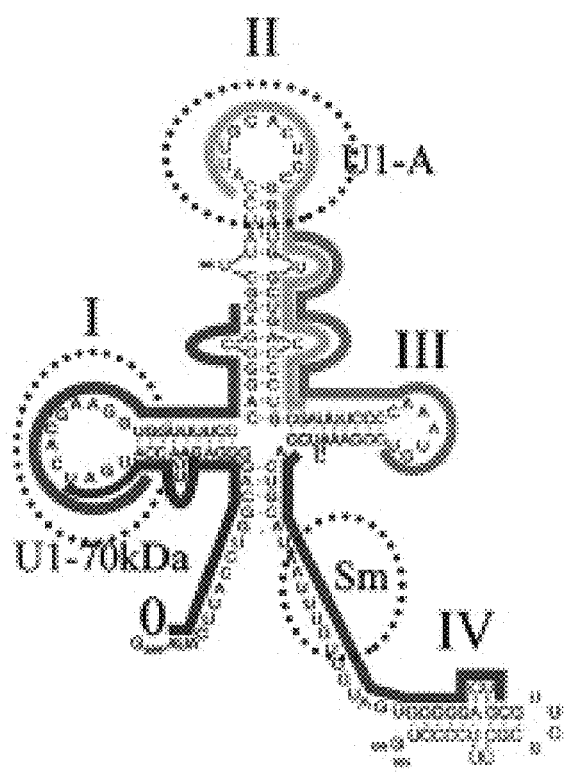
Figure 6:
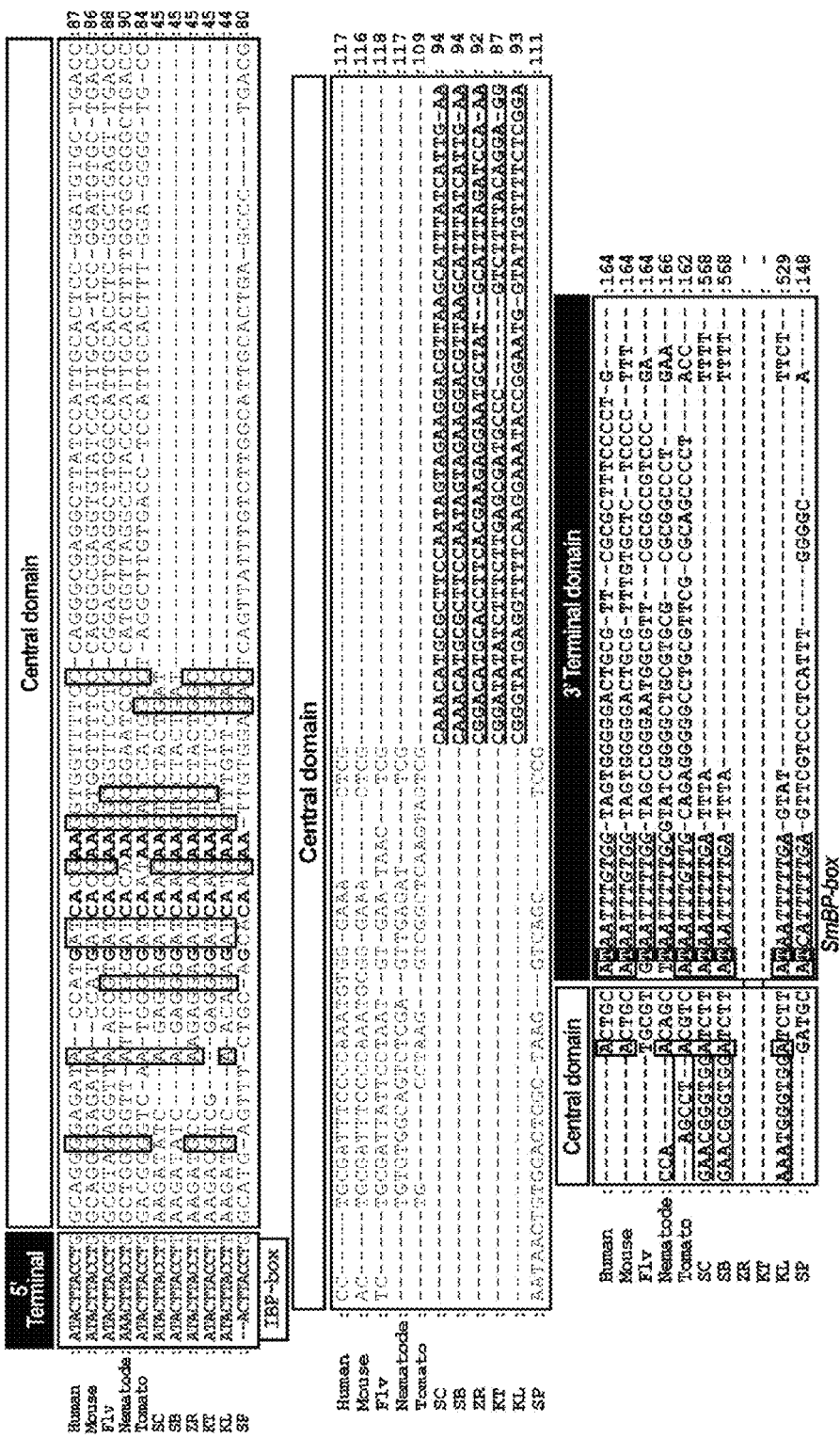
FIG. 6 is a table of alignments of U1 snRNA from different species (Human, SEQ ID NO:6; Mus Musculus, SEQ ID NO:7; Flv, SEQ ID NO:8; Nematode, SEQ ID NO:9; Tomato, SEQ ID NO:10; SC, SEQ ID NO:11; SB, SEQ ID NO:12; ZR, SEQ ID NO:13; KT, SEQ ID NO:14; KL, SEQ ID NO:15; and SP, SEQ ID NO:16).

As used herein a "UVB U1 snRNA" refers to a fragment or fragments of U1 snRNA resulting from photo-cleavage of U1 snRNA. For example, as shown in scheme I of FIG. 5B, photocleavage results in a number of fragments. Useful fragments in the methods and compositions of the disclosure comprise from about 10-100 nucleotides in length. In one embodiment, the fragments comprise (i) a fragment of a loop "a" sequence: GGGAGAACCAUGAUCACGAAG-GUGGUUUUCCC (SEQ ID NO:2) from 10-32 nucleotides; (ii) a fragment of a loop "b" sequence: GGGCGAGGCU-UAUCCAUUGCACUCCGGAUGUGCUGACCCC (SEQ ID NO:3) from 10-40 nucleotides; (iii) a fragment of a loop "c" sequence: CGAUUUCCCCAAAUGUGGGAAACUCG (SEQ ID NO:4) from 10-26 nucleotides in length; (iv) a fragment of a loop "d" sequence UAGUCCCCCACUGCG-UUCGCGCUUUCCCCUG(SEQ ID NO:5) from 10-31 nucleotides in length; (v) any of the foregoing sequences wherein U is T; (vi) complements of any of the foregoing sequences; and (vii) any of the foregoing sequences comprising a non-natural nucleotide. In addition, the term UVB U1 snRNA includes polynucleotides of 10 to 100 (e.g., 10, 20, 30, 40, 50, 60, 70, 80 or 90) nucleotides in length comprising 90-99% identity with SEQ ID NO:1 and oligonucleotides comprising from 90-99% sequence identity to SEQ ID NO:2, 3, or 4 and having a length of about 10-40 nucleotides in length, wherein the polynucleotide or oligonucleotide can stimulate IL-6 and/or TNFα production. For example, using the table in FIG. 6 comprising an alignment of U1 snRNA sequences from different species, one of skill in the art can readily identify sequence that have sufficient identity to SEQ ID NO:1, 2, 3, or 4 from other species or which can be synthesized and used in the methods and compositions of the disclosure. In another embodiment, the disclosure provides a composition comprising a polynucleotide having at least one modified nucleic acids with at least 80% identity to U1 snRNA exposed to UVB.

The term "isolated" as used herein refers to a nucleic acid that is substantially free of proteins, lipids, and other nucleic acids with which an in vivo-produced nucleic acids naturally associated. Typically, the nucleic acid is at least 70%, 80%, 90% or more pure by weight, and conventional methods for synthesizing nucleic acids in vitro can be used in lieu of in vivo methods. As used herein, "nucleic acid" or "polynucleotide" or "oligonucleotide" refers to a polymer of deoxyribonucleotides or ribonucleotides, in the form of a separate fragment or as a component of a larger genetic construct (e.g., by operably linking a promoter to a nucleic acid encoding a peptide of the disclosure). Numerous genetic constructs (e.g., plasmids and other expression vectors) are known in the art and can be used to produce the polynucleotides, oligonucleotides of polypeptides of the disclosure in cell-free systems or prokaryotic or eukaryotic (e.g., yeast, insect, or mammalian) cells. By taking into account the degeneracy of the genetic code, one of ordinary skill in the art can readily synthesize nucleic acids of the disclosure. The nucleic acids of the disclosure can readily be used in conventional molecular biology methods.

Polynucleotides or oligonucleotides comprising a UVB U1 snRNA or encoding a polypeptide antagonist of the disclosure can be inserted into an "expression vector." The term "expression vector" refers to a genetic construct such as a plasmid, virus or other vehicle known in the art that can be engineered to contain a polynucleotide or oligonucleotide to be expressed or delivered. Such expression vectors are typically plasmids that contain a promoter sequence that facilitates transcription of the inserted genetic sequence in a host cell. The expression vector typically contains an origin of replication, and a promoter, as well as genes that allow phenotypic selection of the transformed cells (e.g., an antibiotic resistance gene). Various promoters, including inducible and constitutive promoters, can be utilized in the disclosure. Typically, the expression vector contains a replicon site and control sequences that are derived from a species compatible with the host cell.

Transformation or transfection of a host cell with a polynucleotide of the disclosure can be carried out using conventional techniques well known to those skilled in the art. For example, where the host cell is *E. coli*, competent cells that are capable of DNA uptake can be prepared using the $CaCl_2$, $MgCl_2$ or RbCl methods known in the art. Alternatively, physical means, such as electroporation or microinjection can be used. Electroporation allows transfer of a polynucleotide into a cell by high voltage electric impulse. Additionally, polynucleotides can be introduced into host cells by protoplast fusion, using methods well known in the art. Suitable methods for transforming eukaryotic cells, such as electroporation and lipofection, also are known.

"Host cells" encompassed by of the disclosure are any cells in which the polynucleotides of the disclosure can be used. The term also includes any progeny of a host cell. Host cells, which are useful, include bacterial cells, fungal cells (e.g., yeast cells), plant cells and animal cells. For example, host cells can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection; DEAE-Dextran mediated transfection or electroporation (Davis, L., Dibner, M., Battey, I., Basic Methods in Molecular Biology (1986)). As representative examples of appropriate hosts, there may be mentioned: fungal cells, such as yeast; insect cells such as Drosophila S2 and Spodoptera Sf9; animal cells such as CHO, COS or Bowes melanoma; plant cells, and the like. The selection of an appropriate host is deemed to be within the scope of those skilled in the art from the teachings herein.

Host cells can be eukaryotic host cells (e.g., mammalian cells). In one aspect, the host cells are mammalian production cells adapted to grow in cell culture. Examples of such cells commonly used in the industry are CHO, VERO, BHK, HeLa, CV1 (including Cos; Cos-7), MDCK, 293, 3T3, C127, myeloma cell lines (especially murine), PC12 and W138 cells.

Polynucleotides encoding agonist or antagonists of the disclosure can be isolated from a cell (e.g., a cultured cell), or they can be produced in vitro.

Polynucleotides and oligonucleotides used in the methods and compositions of the disclosure include naturally occurring, synthetic, and intentionally manipulated polynucleotides. A UVB U1 snRNA oligonucleotides of the disclosure also includes those oligonucleotides capable of hybridizing, under stringent hybridization conditions, to sequences consisting of SEQ ID NO:1, 2, 3, or 4, above. "Stringent hybridization conditions" refers to an overnight incubation at 42° C. in a solution comprising 50% formamide, 5.times.SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C. It will be recognized that a UVB U1 snRNA of the disclosure, may be operably linked to a second heterologous polynucleotide such as a promoter or a heterologous sequence encoding a desired peptide or polypeptide sequence.

The disclosure demonstrates that UVB U1 snRNA is an inducer of inflammation by activating TLR3 and producing TNF-alpha and/or IL-6. Although the compositions of the disclosure where identified using UV irradiation to induce inflammation, often considered a deleterious effect, the use of UVB U1 snRNA can be used to promote inflammation wherein such inflammation is beneficial to prevent, for example, infection, to fight infection, or to promote anti-cancer effects.

For example, agonist of UVB U1 snRNA including UVB U1 snRNA can be used to treat bacterial infection, fungal infections and viral infections by promoting an inflammatory response at the site of infection. Thus the disclosure also provides a method for inhibiting the growth of a bacterium or infection by a bacterium by contacting a tissue subject to infection with or infected with the bacterium with an inhibiting effective amount of a UVB U1 snRNA or agonist of the disclosure. The term "contacting" refers to exposing the tissue to a UVB U1 snRNA or agonist so that the UVB U1 snRNA or agonist can promote an inflammatory response including, for example, recruitment of inflammatory cells. Contacting of an tissue with a UVB U1 snRNA or agonist of the disclosure can occur by contacting the tissue with a pharmaceutical preparation comprising a UVB U1 snRNA or agonist. For example, contacting can occur in vivo, for example by administering the UVB U1 snRNA or agonist to a subject afflicted with a bacterial infection or susceptible to infection. In vivo contacting includes both parenteral as well as topical. "Inhibiting" or "inhibiting effective amount" refers to the amount of UVB U1 snRNA or agonist that is sufficient to cause, for example, a bacteriostatic or bactericidal effect. Infections that can be affected by the UVB U1 snRNA or agonist of the disclosure include infections by both gram-negative and gram-positive bacteria. For example, bacterial infections that can be treated include *Staphylococcus aureus, Streptococcus pyogenes* (group A), *Streptococcus* sp. (viridans group), *Streptococcus agalactiae* (group B), *S. bovis, Streptococcus* (anaerobic species), *Streptococcus pneumoniae*, and *Enterococcus* sp.; Gram-negative cocci such as, for example, *Neisseria gonorrhoeae, Neisseria meningitidis*, and *Branhamella catarrhalis*; Gram-positive bacilli such as *Bacillus anthracis, Bacillus subtilis, P. acne Corynebacterium diphtheriae* and *Corynebacterium* species which are diptheroids (aerobic and anerobic), *Listeria monocytogenes, Clostridium tetani, Clostridium difficile, Escherichia coli, Enterobacter species, Proteus mirablis* and other sp., *Pseudomonas aeruginosa, Klebsiella pneumoniae, Salmonella, Shigella, Serratia*, and *Campylobacter jejuni*. Infection with one or more of these bacteria can result in diseases such as bacteremia, pneumonia, meningitis, osteomyelitis, endocarditis, sinusitis, arthritis, urinary tract infections, tetanus, gangrene, colitis, acute gastroenteritis, impetigo, acne, acne posacue, wound infections, born infections, fascitis, bronchitis, and a variety of abscesses, nosocomial infections, and opportunistic infections. The method for inhibiting the growth of bacteria can also include contacting the tissue with the UVB U1 snRNA or agonist in combination with one or more antibiotics.

Fungal infections may also be affected by the UVB U1 snRNA or agonist of the disclosure and include infections by dermatophytes (e.g., *Microsporum canis* and other *Microsporum* sp.; and *Trichophyton* sp. such as *T. rubrum*, and *T. mentagrophytes*), yeasts (e.g., *Candida albicans, C. Tropicalis*, or other *Candida species*), *Saccharomyces cerevisiae, Torulopsis glabrata, Epidermophyton floccosum, Malassezia furfur* (*Pityropsporon orbiculare*, or *P. ovale*), *Cryptococcus neoformans, Aspergillus fumigatus, Aspergillus nidulans*, and other *Aspergillus* sp., Zygomycetes (e.g., *Rhizopus, Mucor*), *Paracoccidioides brasiliensis, Blastomyces dermatitides, Histoplasma capsulatum, Coccidioides immitis*, and *Sporothrix schenckii*.

In such embodiments, the UVB U1 snRNA can be administered to the skin of a subject in need of such treatment to promote production of inflammatory mediators such as TNF-α and IL-6. As described more fully below, the UVB U1 snRNA serves as an active agent in a pharmaceutical preparation. The pharmaceutical can be administered to the skin topically. In some embodiment, the UVB U1 snRNA is administered in combination with one or more additional agents to promote uptake through the skin and the cells of the skin. Such additional agents include protein transduction domains (e.g., Tat peptides; see, e.g., U.S. Pat. Publ. 2009/0093026A1), liposomal formulation, and charge neutralizing groups linked to the nucleic acid base (see, e.g., U.S. Pat. Publ. 2009/0093425A1, which is incorporated herein by reference in its entirety).

In another embodiment, the disclosure provides compositions (including expression vectors such as viral vectors), nanoparticles, liposomal formulations and other delivery vehicles for delivering a UVB-U1 snRNA fragment to a subject, tissue or cell to promote TNF-alpha production. In one embodiment, the compositions promote inflammation. In another embodiment, the compositions are used to treat a cell proliferative disorder such as cancer.

Thus, the disclosure provides compositions of non-coding U1 small nuclear RNAs (snRNA), and a method to use RNA oligonucleotides as adjuvant therapies to stimulate the inflammatory response for diseases that would respond well to inflammation, such as infectious diseases and cancer.

In another embodiment, anti-RNAs or antibodies against UVB U1 snRNA could be used to block the effects of UVB U1 snRNA. In another embodiment, TLR3 antagonists (e.g., antibodies against TLR3 or ligand fragments that inhibit TLR3 activity could be used to reduce solar aging and attenuate inflammation from sunburn or other forms of tissue necrosis such as injury and radiation. For example, agents that inhibit the activity of UVB U1 snRNA can be used to treat inflammation including, but not limited to, acne and rosacea, atopic dermatitis, contact dermatitis, drug eruptions, psoriasis, seborrheic dermatitis, connective tissue diseases (such as lupus, scleroderma, and rheumatoid arthritis), other autoimmune disorders such as the blistering disease bullous pemphigoid or pemphigus, pigmentary diseases (such as post inflammatory hyperpigmentation, melasma and vitiligo), urticaria or hives, inflammation associated with skin infections such as tinea corporis or fungal infection of the finger or toenails, among others.

In yet another embodiment, compositions comprising agonistic activity U1 snRNA are provided and methods of use thereof. Such compositions include isolated U1 snRNA, modified U1 snRNA and polynucleotides having 90% or greater identity (e.g., 91, 92, 93, 94, 95, 96, 97, 98, or 99% identity to a sequence consisting of SEQ ID NO:1. An agonist of U1 snRNA can be used to treat inflammatory disease and disorders including, but not limited to, psoriasis and itch. For example, the disclosure contemplates administering a U1 snRNA agonist to a subject suffering from psoriasis alone or in combination with a UVB U1 snRNA antagonist. In some embodiments, the method may include phototherapy or other anti-inflammatory therapy. The method includes administering the U1 snRNA agonist topically to a subject at a site to be treated (e.g., a psoriasis or itch site on the skin).

As will be apparent from the disclosure herein, UV damage to non-coding RNA serves as a warning signal against high levels of solar exposure. UVB alters cellular U1 snRNA and this molecule can serve as an endogenous danger signal that UV damage has occurred.

In another embodiment, the disclosure provides a method of identifying an inflammatory skin disease comprising measuring the presence of UVB U1 snRNA in a tissue sample. The UVB U1 snRNA can be identified using primers and probes that specifically hybridize to such oligonucleotides. Other methods for detecting UVB U1 snRNA in a sample will be readily apparent to one of skill in the art including, but not limited to, ELISA assays, Northern Blot assays, sequencing, gel chromatography, and mass spectroscopy. In such assays, fragments of U1 snRNA are identified. Typically, such an assay will be used on subjects that have an unknown etiology of skin inflammation.

The disclosure also provide a method of identifying agonist and antagonists of skin-associated inflammation comprising contacting a tissue comprising U1 snRNA and/or a TLR3 receptor with a potential agonist or antagonist and measuring (i) the production of UVB-U1 snRNA products upon exposure or non-exposure to UV light (e.g., UVB) or (ii) the production of TNF-α and/or IL-6; wherein an agonist is a compound that (a) promotes UVB-U1 snRNA in the tissue in the presence or absence of UV light or (b) promotes TNF-α and/or IL-6 production and wherein an antagonist is a compound that (a) inhibits UVB-U1 snRNA production in the tissue when exposed to UV light or (b) inhibits production of TNF-α and/or IL-6.

A pharmaceutical composition according to the disclosure can be in a form suitable for administration to a subject using carriers, excipients, and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, chelating agents, and inert gases. Other pharmaceutically acceptable carriers include aqueous solutions, non-toxic excipients, including salts, preservatives, buffers and the like, as described, for instance, in Remington's Pharmaceutical Sciences, 15th ed., Easton: Mack Publishing Co., 1405-1412, 1461-1487 (1975), and The National Formulary XIV., 14th ed., Washington: American Pharmaceutical Association (1975), the contents of which are hereby incorporated by reference. The pH and exact concentration of the various components of the pharmaceutical composition are adjusted according to routine skills in the art. See Goodman and Gilman's, The Pharmacological Basis for Therapeutics (7th ed.).

The pharmaceutical compositions according to the disclosure may be administered locally or systemically. A "therapeutically effective dose" is the quantity of an agent according to the disclosure necessary to prevent, to cure, or at least partially arrest the symptoms of a bacterial infection. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of infections. Various considerations are described, e.g., in Langer, Science, 249: 1527, (1990); Gilman et al. (eds.) (1990), each of which is herein incorporated by reference.

As used herein, "administering a therapeutically effective amount" is intended to include methods of giving or applying a pharmaceutical composition of the disclosure to a subject that allow the composition to perform its intended therapeutic function. The therapeutically effective amounts will vary according to factors, such as the degree of infection in a subject, the age, sex, and weight of the individual. Dosage regima can be adjusted to provide the optimum therapeutic response. For example, several divided doses can be administered daily or the dose can be proportionally reduced as indicated by the exigencies of the therapeutic situation.

The pharmaceutical composition can be administered in a convenient manner, such as by injection (subcutaneous, intravenous, etc.), oral administration, inhalation, transdermal application, topically, or rectal administration. Depending on the route of administration, the pharmaceutical composition can be coated with a material to protect the pharmaceutical composition from the action of enzymes, acids, and other natural conditions that may inactivate the pharmaceutical composition. The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. In all cases, the composition should be sterile and should be fluid to the extent that easy syringability exists. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be typical to include isotonic agents, for example, sugars, polyalcohols, such as mannitol, sorbitol, or sodium chloride in the composition. Prolonged absorption of the injectable compositions can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle that contains a basic dispersion medium and the required other ingredients from those enumerated above.

The pharmaceutical composition can be orally administered, for example, with an inert diluent or an assimilable edible carrier. The pharmaceutical composition and other ingredients can also be enclosed in a hard or soft-shell gelatin capsule, compressed into tablets, or incorporated directly into the individual's diet. For oral therapeutic administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5% to about 80% of the weight of the unit.

The tablets, troches, pills, capsules, and the like can also contain the following: a binder, such as gum gragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Of course, any material used in preparing any dosage unit form should be pharmaceutically pure and substantially non-toxic/biocompatible in the amounts employed. In addition, the pharmaceutical composition can be incorporated into sustained-release preparations and formulations.

Thus, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the pharmaceutical composition, use thereof in the therapeutic compositions and methods of treatment is contemplated. Supplementary active compounds can also be incorporated into the compositions.

It is especially advantageous to formulate parenteral compositions in dosage unit form for ease of administration and uniformity of dosage. "Dosage unit form" as used herein, refers to physically discrete units suited as unitary dosages for the individual to be treated; each unit containing a predetermined quantity of pharmaceutical composition is calculated to produce the desired therapeutic effect in association with the required pharmaceutical carrier. The specification for the dosage unit forms of the disclosure are related to the characteristics of the pharmaceutical composition and the particular therapeutic effect to be achieve.

The principal pharmaceutical composition is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

EXAMPLES

To investigate how human skin detects acutely damaging levels of UVB radiation, experiments were performed to determine if there was a transferrable signal for inflammation immediately after UVB exposure. Cultured primary human keratinocytes were exposed to UVB (15 mJ/cm$^2$), then these irradiated cells, or control non-irradiated cells, were immediately lysed and frozen or immediately injected intradermally into mouse ears. Cells that were previously irradiated induced erythema, increased ear thickness and increased TNF-α and IL-6, while equal numbers of non-irradiated sonicated cells did not (FIG. 1a-d). The response to UV treated cells was found to be dependent on TLR3 signaling since similar experiments done with TLR3$^{-/-}$ mice showed a greatly decreased inflammatory response and lacked a detectable increase in TNF-α and IL-6 (FIG. 1a-d). Mice without functional TRIF, an essential downstream element in TLR3 signaling, also did not respond. Targeted knockdown of TLR3 in cultured keratinocytes by siRNA (FIG. 1e) also attenuated the TNF-α (FIG. 1f, g) and IL-6 response to the irradiated cells. Since TLR3 is a pattern recognition molecule best known for its ability to detect dsRNA, it was hypothesized that the product of UVB irradiated cells that triggered inflammation was endogenous RNA. To test this, cells were treated with RNase after irradiation and before addition to non-irradiated cells. RNAse treatment attenuated the induction of TNF-α, and IL-6, by both keratinocytes and monocytes (FIG. 1h, i, j). Thus, these data supported the hypothesis that inflammation after UVB exposure is mediated by a change in RNA following irradiation.

Figure 2:
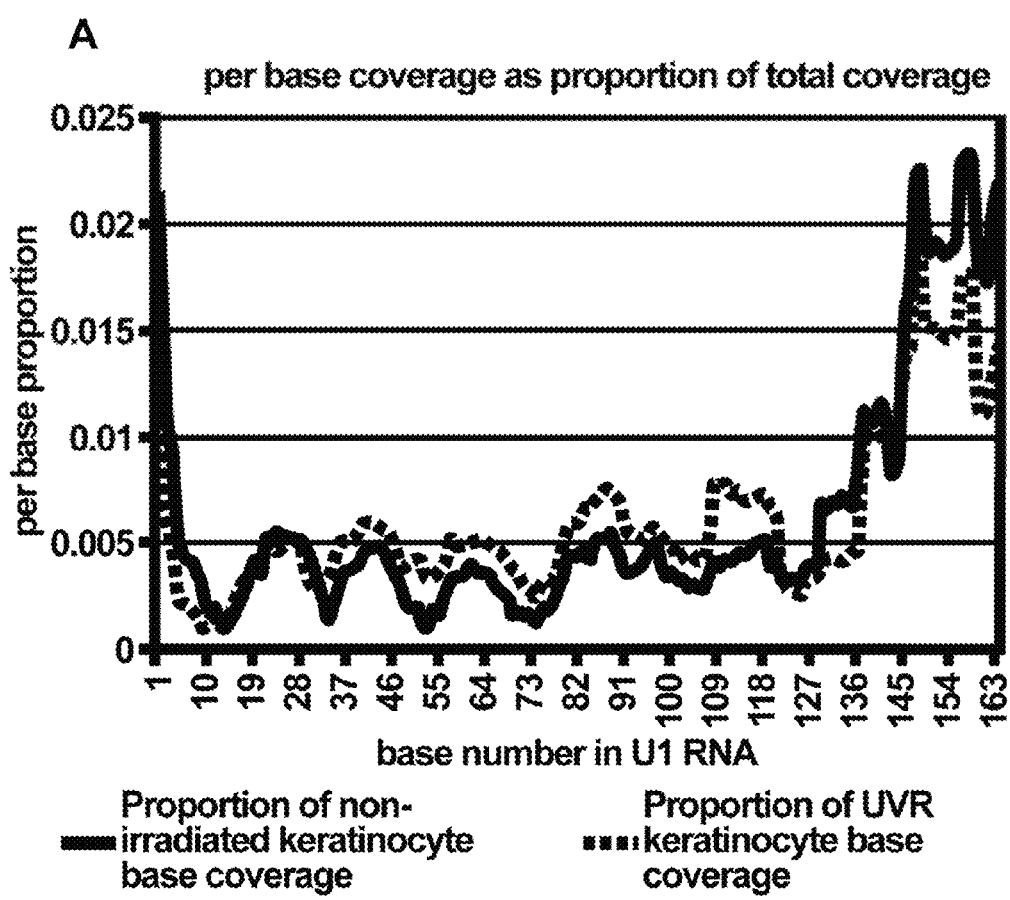
FIG. 2A-H shows the identification of U1 RNA as an inducer of inflammation after UVB radiation. (A) Per base coverage as a proportion of total coverage in sonicated keratinocytes and UVR keratinocytes. (B) U1 RNA representation (SEQ ID NO:1 from by 2-165) of RNA-sequencing analysis of base coverage to show UVR keratinocyte proportion of reads over sonicated keratinocyte proportion of reads. Ratio increases from blue to red. Stem loops are numbered A-B. (C) Relative abundance of U1 RNA greater than and less than 100 nucleotides (nt). (D) qRT-PCR analysis of TNF-α in NHEK 24 hr following addition of 100 ng of U1 RNA treated with 15 mJ/cm$^2$ UVB. ($*p<0.05$). ELISA analysis of TNF-α released into NHEK media (E) ($*p<0.05$) or PBMC media (F) ($**p<0.01$) 24 hr following U1 RNA treatment. (G) ELISA analysis of TNF-α following treatment with UVB U1 RNA <100 nt ($*p<0.05$). (H) qRT-PCR analysis of TNF-α following keratinocyte treatment with oligonucleotides complementary to loop a ($*p<0.05$), loop b ($**p<0.01$), loop c ($*p<0.05$), and loop d of U1 RNA.
Figure 2:
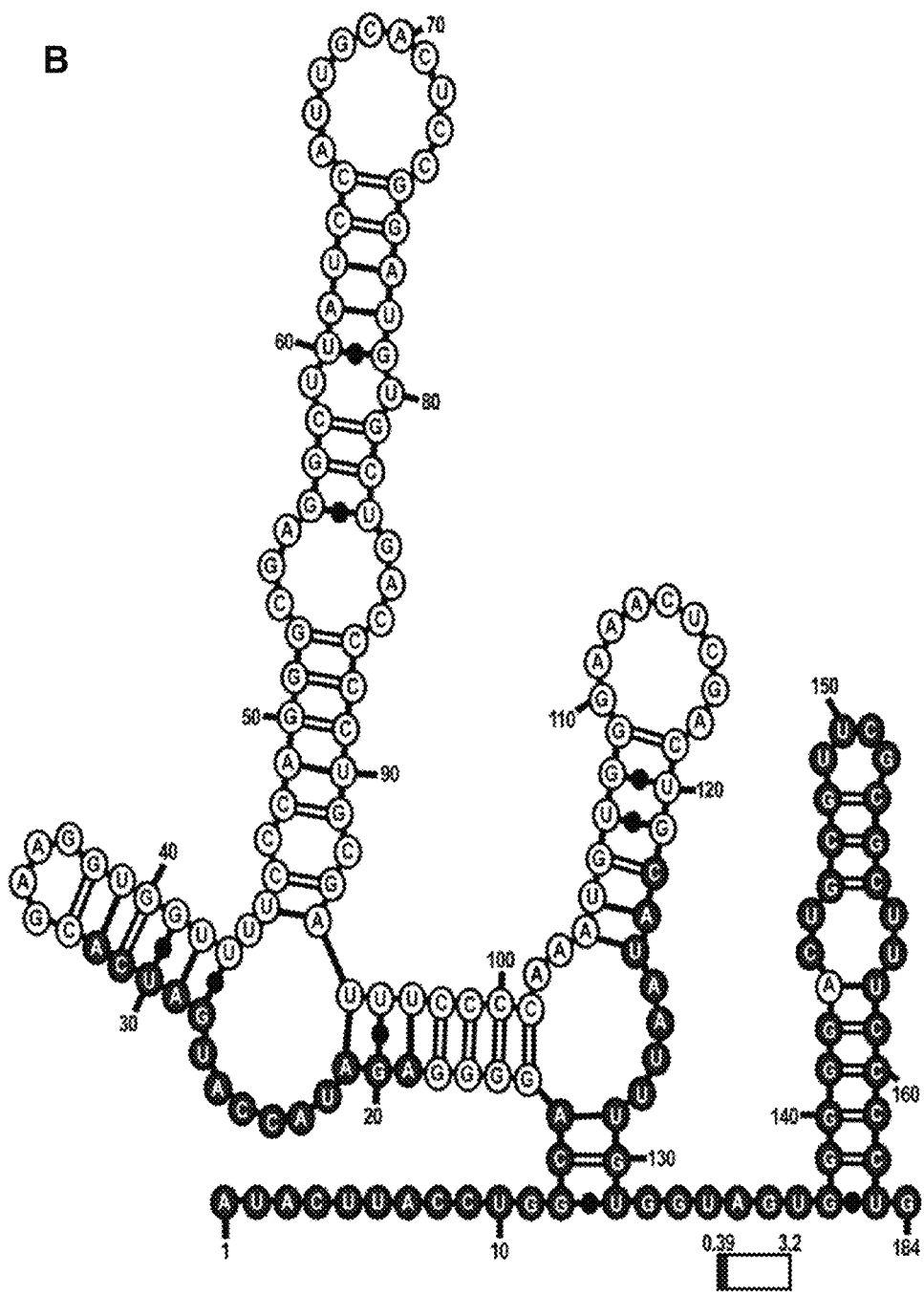
Figure 2:
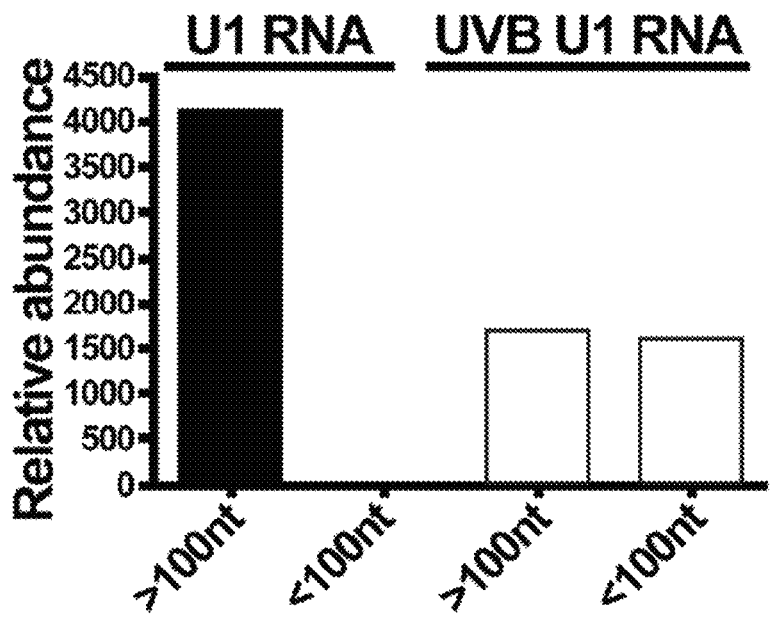
Figure 2:
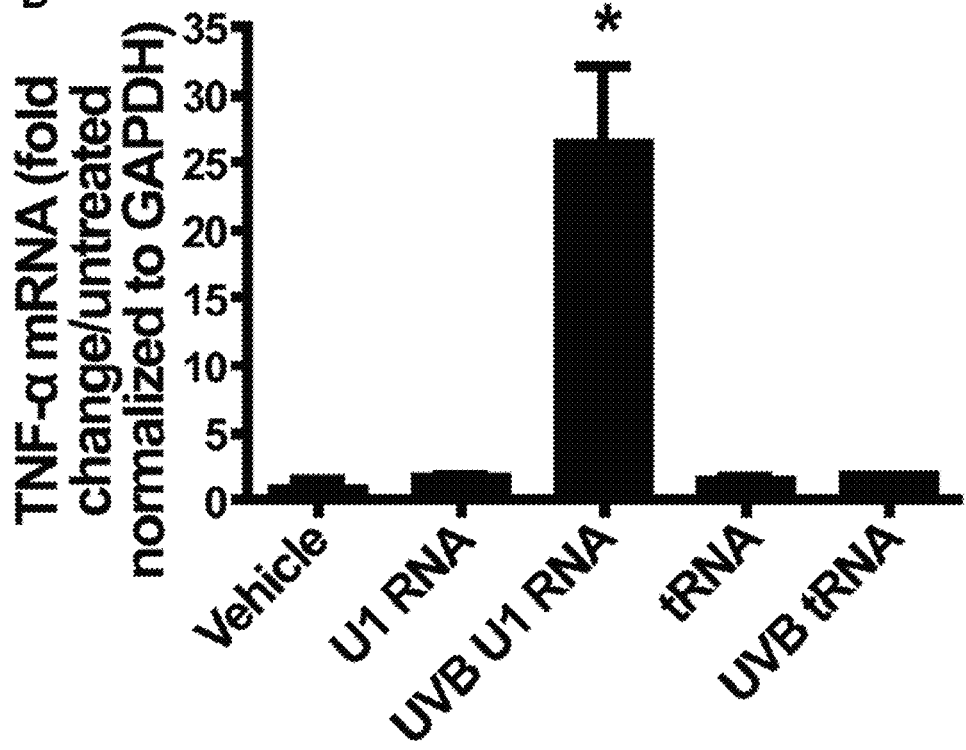
Figure 2:
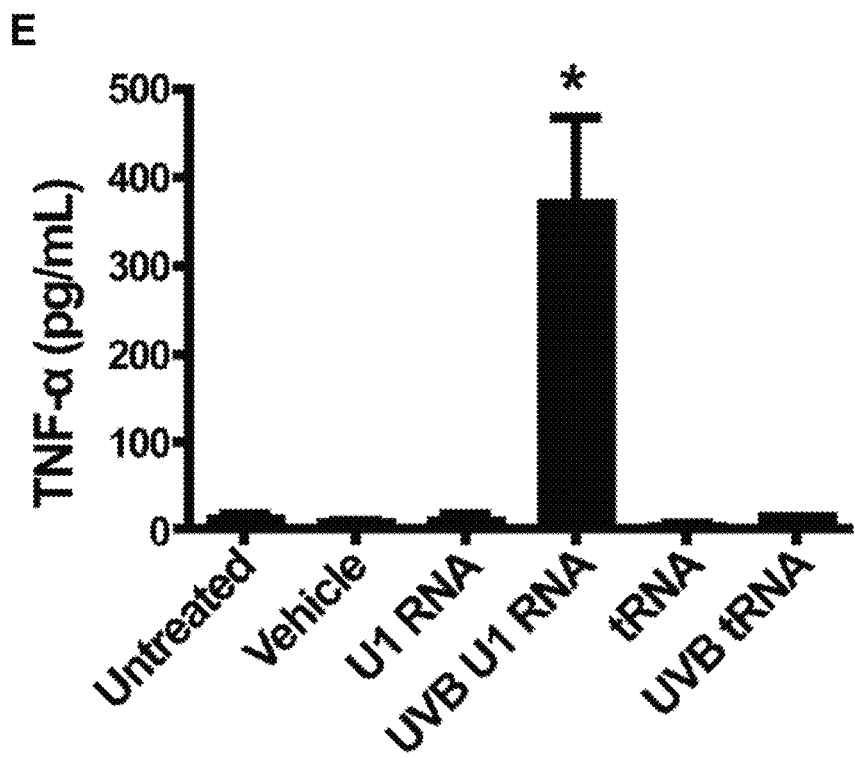
Figure 2:
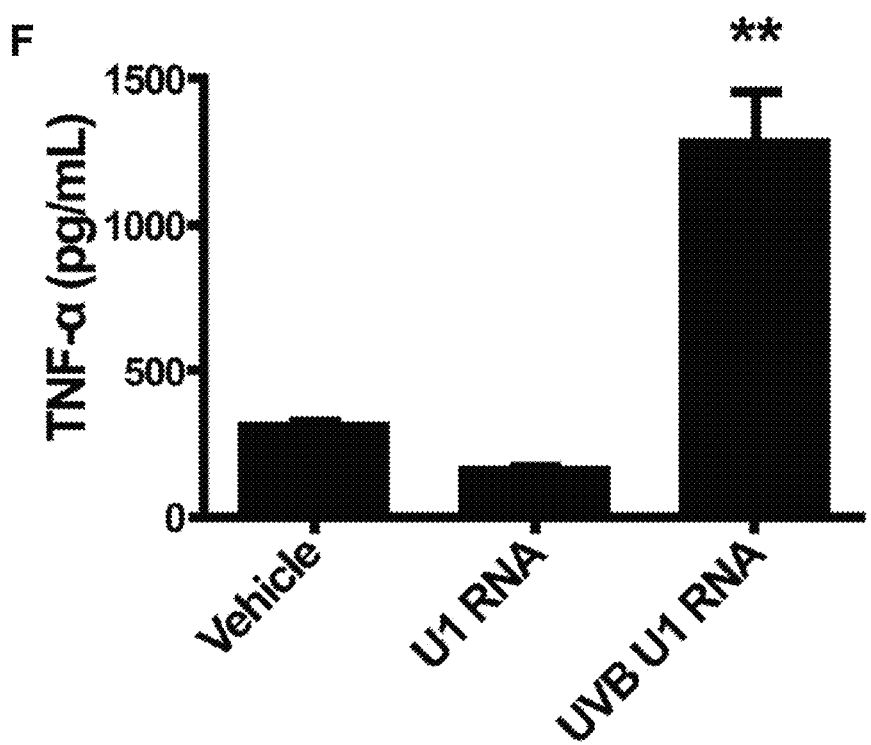
Figure 2:
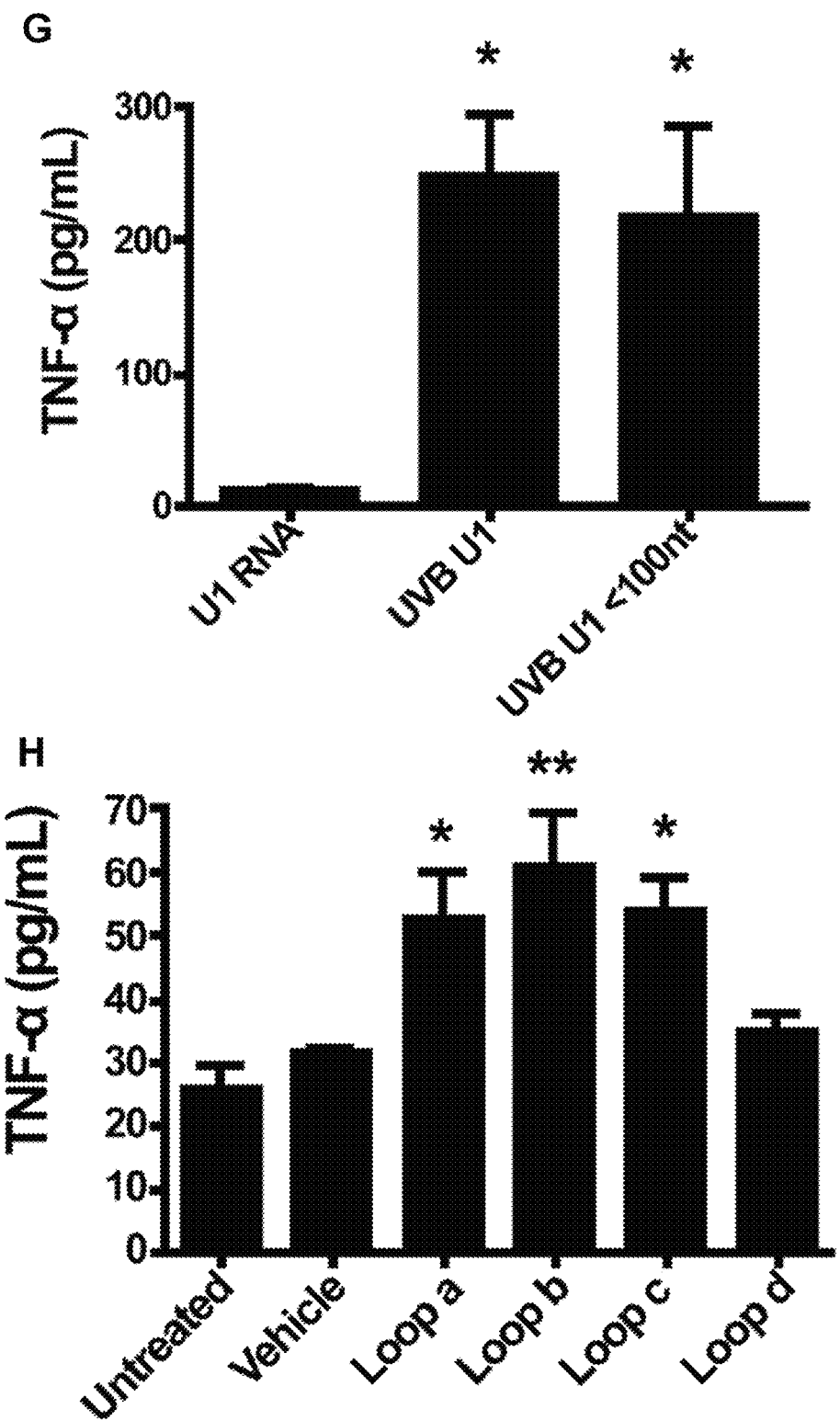

To identify the RNA species that could trigger inflammation a novel adaptation of next-generation whole transcriptome shotgun sequencing (RNA-Seq) was used to analyze the whole transcriptome of UVR keratinocytes. As this method of RNA sequencing is known to be sensitive to RNA structure for primer hybridization, it was reasoned that changes in RNA induced by direct UVB damage would be detectable by an immediate change in frequency of sequence reads. Analysis was performed of primary human keratinocytes immediately after exposure to 15 mJ/cm$^2$ UVB compared to an identical paired unexposed culture. This analysis highlighted the abundant presence of non-coding RNAs and demonstrated that U1 small nuclear (sn) RNA was among the most abundant RNAs (94$^{th}$-percentile) in both irradiated and non-irradiated keratinocytes, and that the sequencing coverage of U1 RNA changed immediately after UVB exposure (FIG. 2a). This non-coding RNA was of particular interest because of its abundance, high frequency of change in sequence reads and prior literature suggesting a role for U1 RNA in initiating auto-immune inflammatory responses. Analysis of U1 RNA structural domains overrepresented following UV exposure demonstrated that the double-stranded base pairs at loops a, b, c became over-represented following irradiation (FIG. 2b). As predicted, gel purification (FIG. 2c), or capillary electrophoresis by Bioanalyzer, of synthetic U1 RNA after irradiation confirmed UVB directly altered its structure and fragmented this non-coding RNA.

Figure 7A:
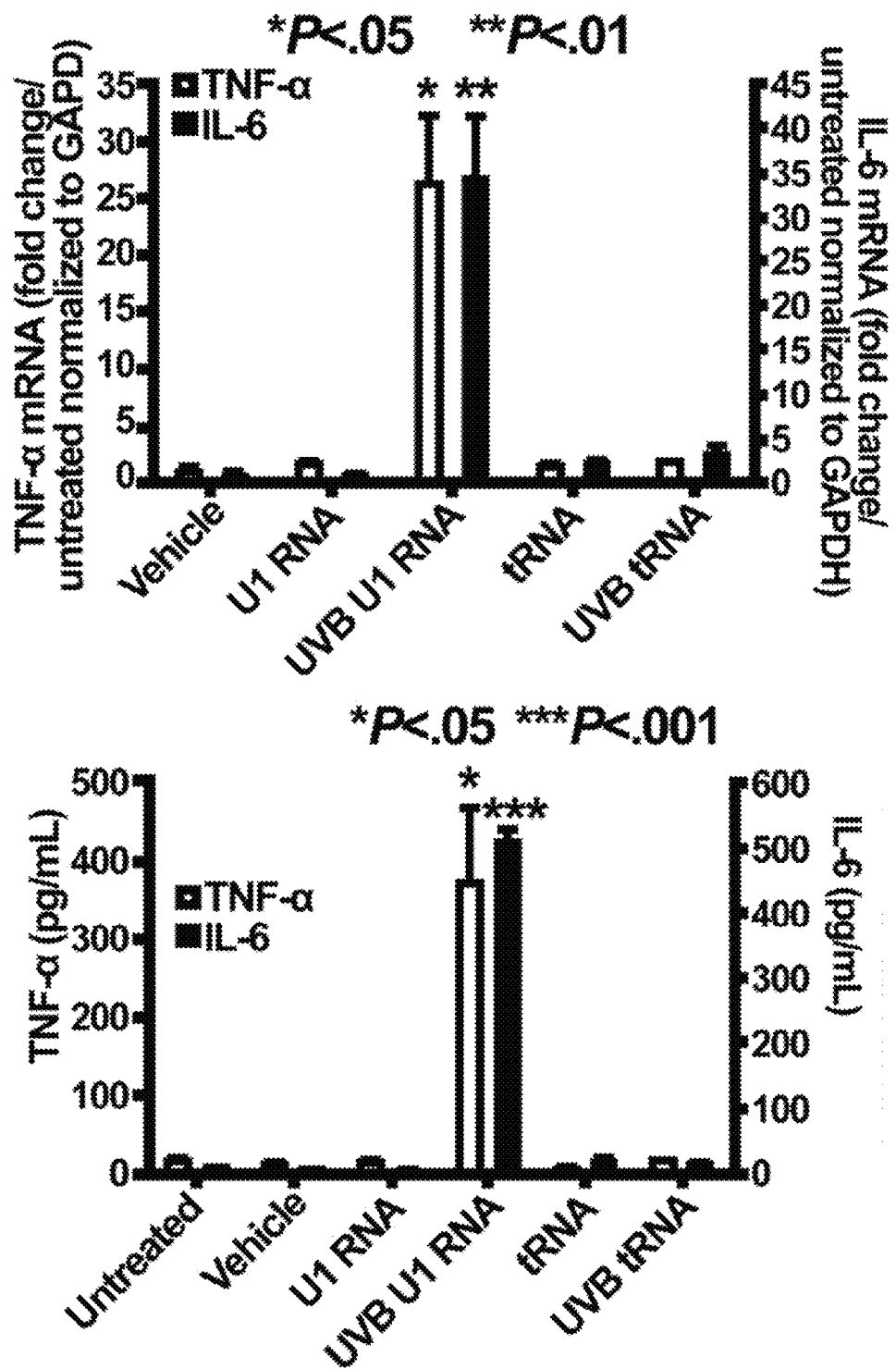
FIG. 7A-B shows that U1 RNA increases inflammatory cytokines. (A) Shows that U1 RNA exposed to UVB significantly increased TNF-α and IL-6. (B) Shows fragments of U1 RNA less than 100 nucleotides are potent stimuli of TNF-α.
Figure 7B:
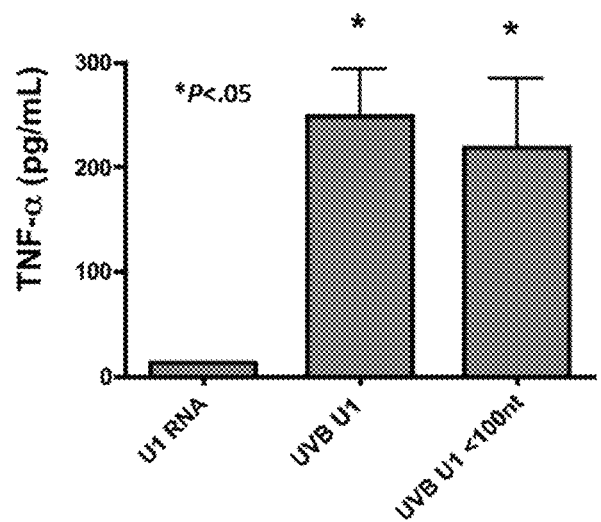
Figure 8:
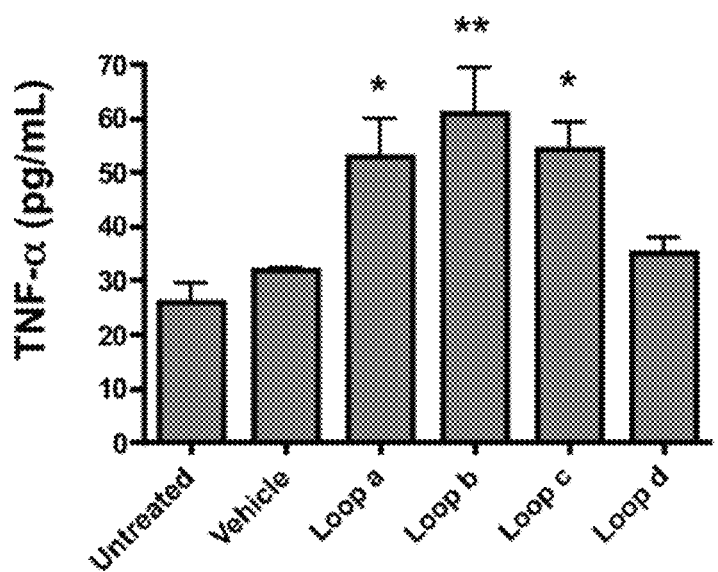
FIG. 8 show that synthetic oligonucleotides based upon loops a, b and c (see FIG. 5A) induced TNF-α.

To test the hypothesis that UV-damaged U1 RNA initiates inflammation, synthetic U1 RNA was assayed for the capacity to trigger cytokine responses. Non-irradiated U1 RNA had no effect on cytokine production when added to cells at concentrations from 100-3000 ng/mL, but U1 RNA (100 ng/mL) exposed to UVB (15 mJ/cm$^2$) significantly increased TNF-α (FIG. 2d-f, 7A) and IL-6 (FIG. 7A) in both keratinocytes and PBMCs. Assay of gel purified U1 RNA after UVB showed the newly generated fractions of less than 100 nucleotides were potent stimuli of TNF-α (FIGS. 2g and 7B). Furthermore, synthetic oligonucleotides representing only the stem loos fragments of U1 RNA predicted by in RNA-Seq analysis (loops a, b, c) directly induced TNF-α (FIGS. 2h and 8). Thus, these data show UVB alters cellular U1 RNA and that this molecule can serve as an endogenous danger signal that UV damage has occurred.

Figure 3:
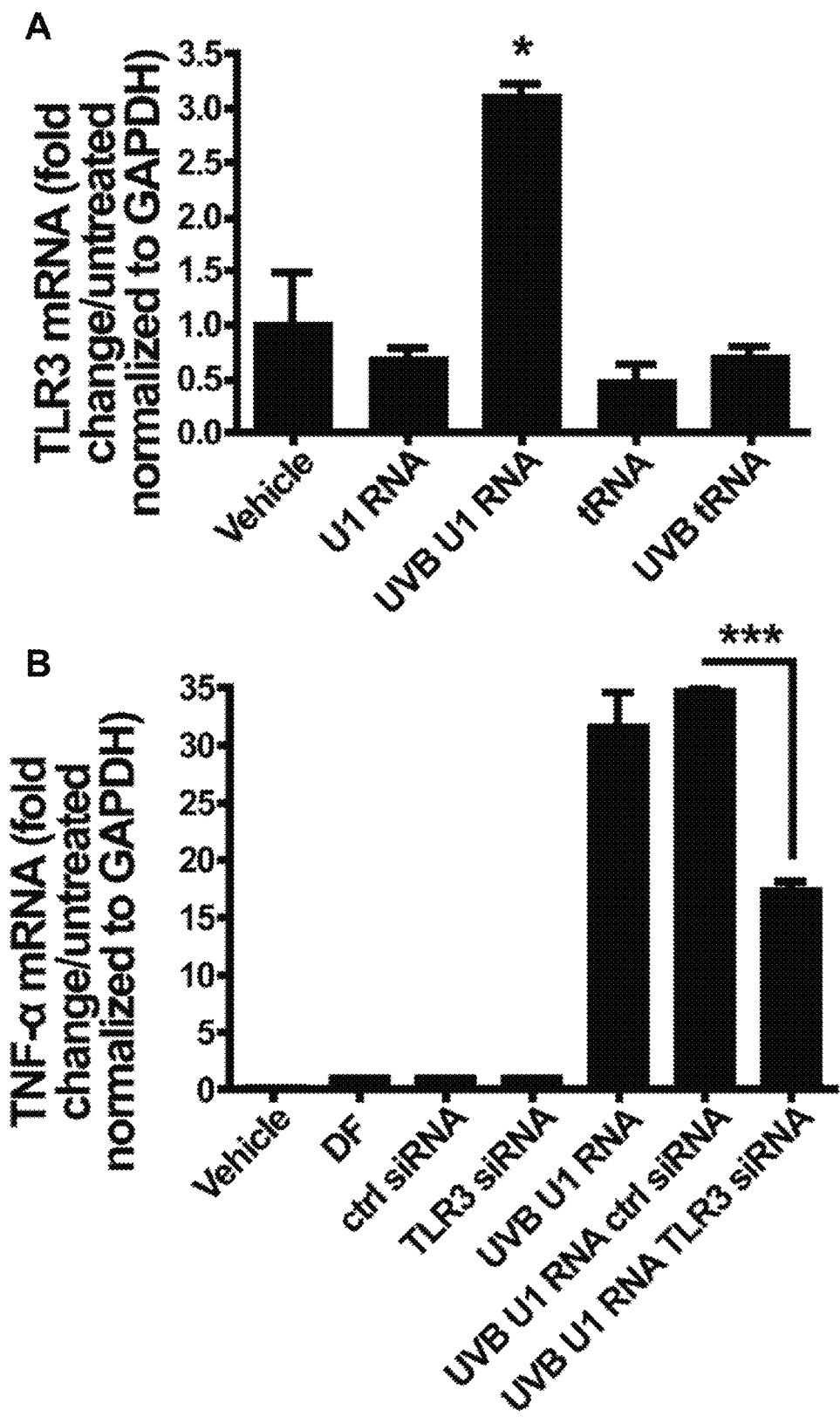
FIG. 3A-E shows the identification of U1 RNA as an inducer of inflammation after UVB radiation. (A) qRT-PCR analysis of TLR3 mRNA expression by NHEK following 24 hrs of culture with U1 RNA. ($*p<0.05$). (B) qRT-PCR analysis of TNF-α from keratinocytes expressing TLR3 siRNA constructs after 24 hrs of culture with U1 RNA. ($***p<0.001$). (C) ELISA analysis of TNF-α from keratinocytes expressing TLR3 siRNA constructs after 24 hrs of culture with U1 RNA. ($*p<0.05$). (D) Fluorescence microscopy of NHEKs treated with U1 RNA for 4 hr. Red staining is RelA/p65 and blue staining is DAPI. Arrows indicate nuclear localization of RelA/p65 following UVB U1 RNA treatment. (E) Western blot of nuclear lysates of keratinocytes treated with UVB U1 RNA for 1, 2, and 4 hrs for RelA/p65 and Lamin B1 (loading control).
Figure 3:
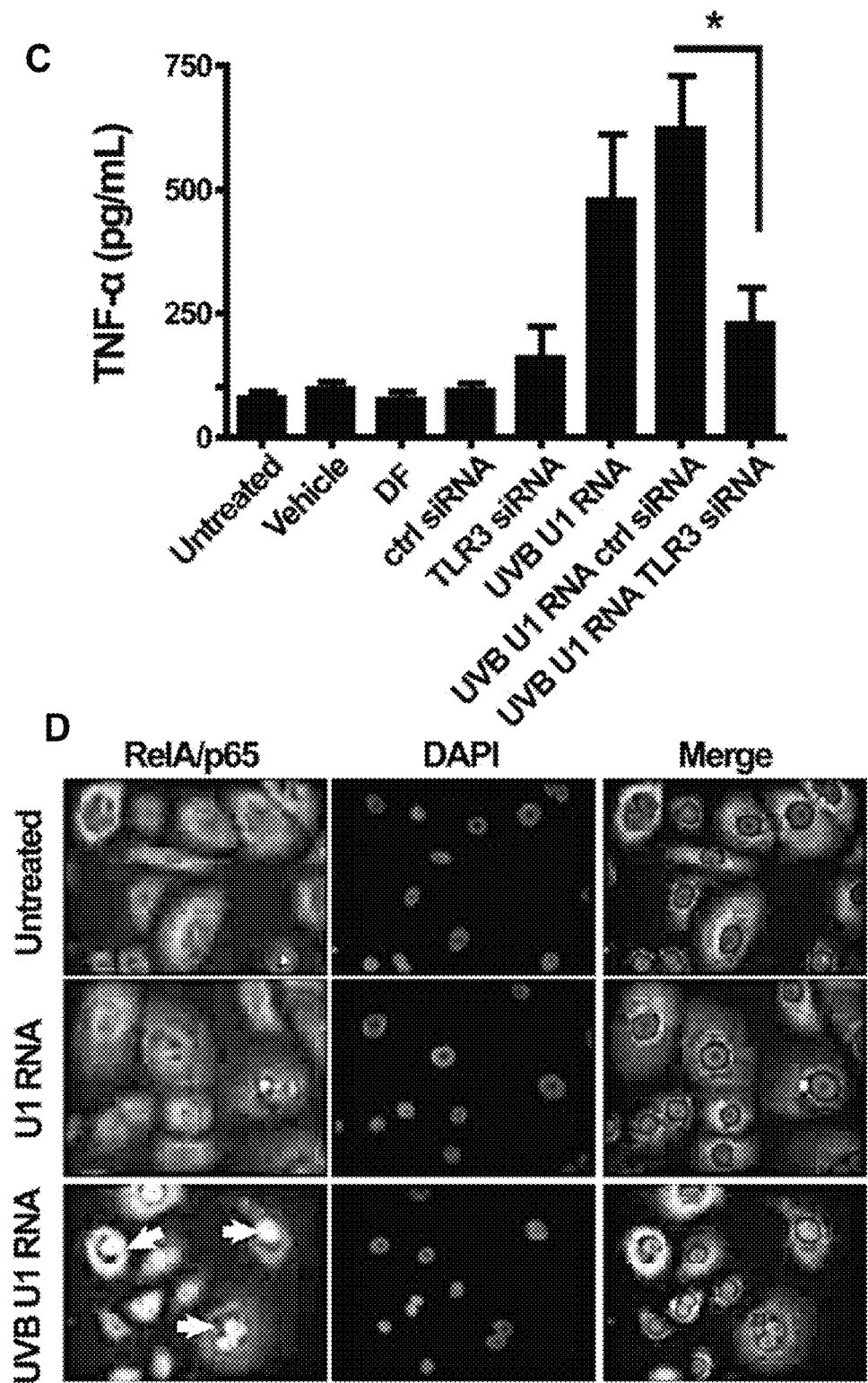
Figure 3:
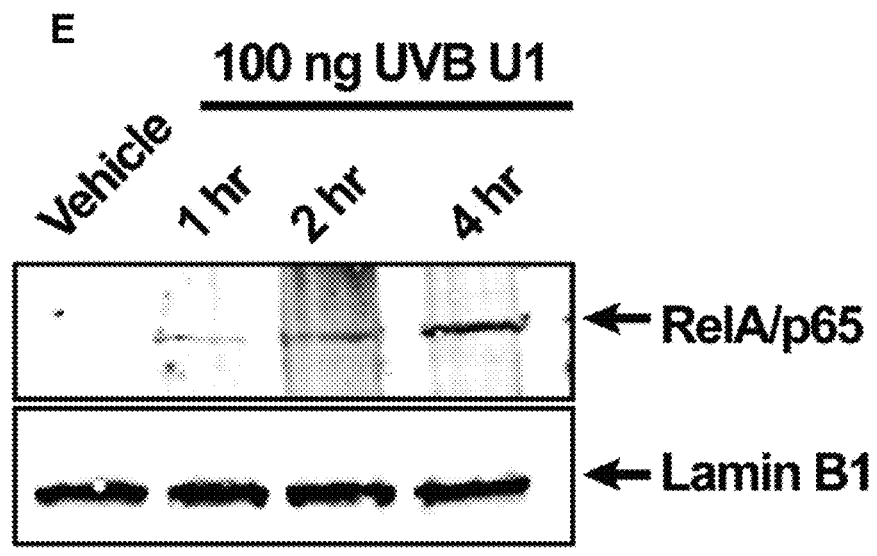
Figure 9:
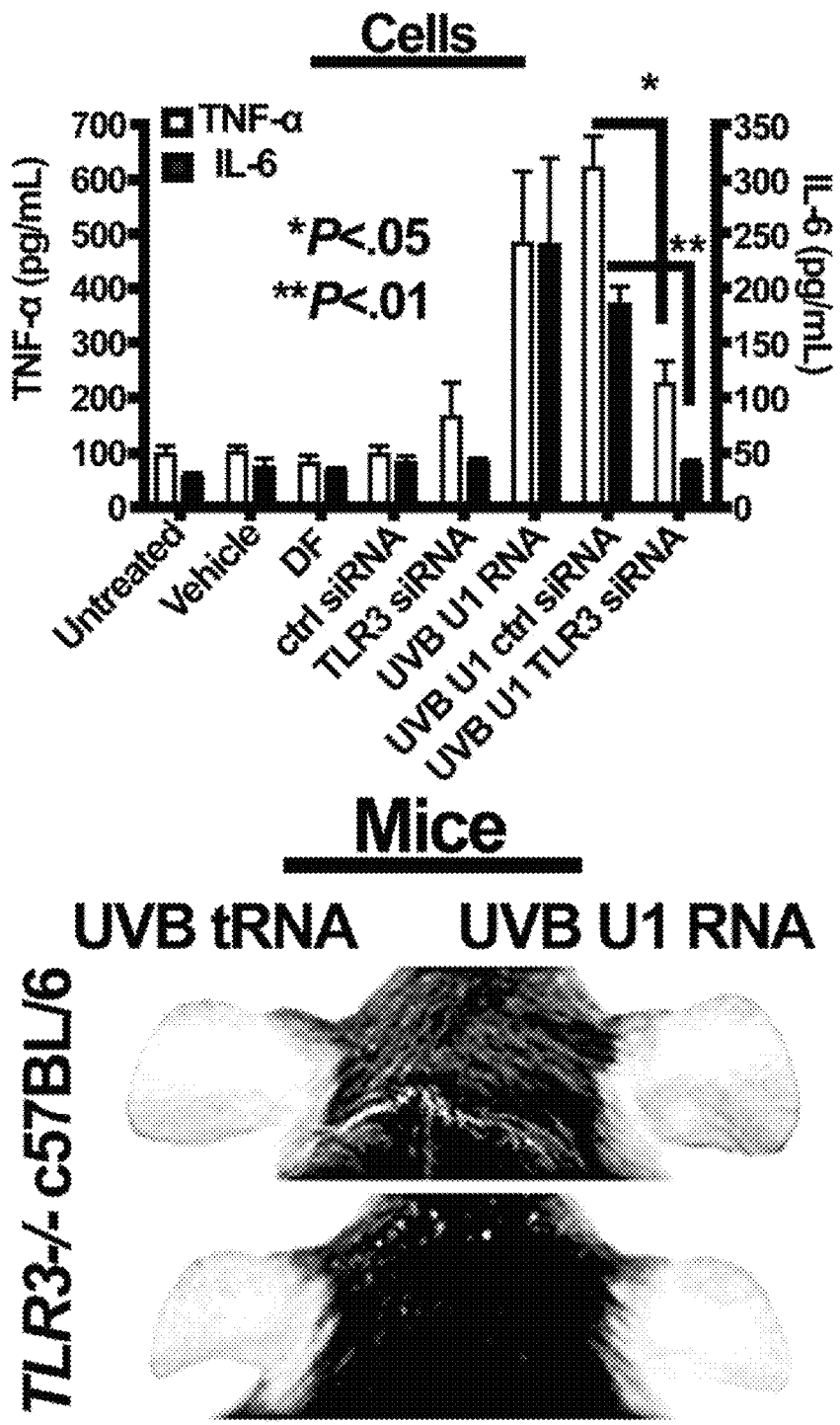
FIG. 9 shows that TLR3 is essential for the cytokine response to U1 RNA and UVB damage.
Figure 9:
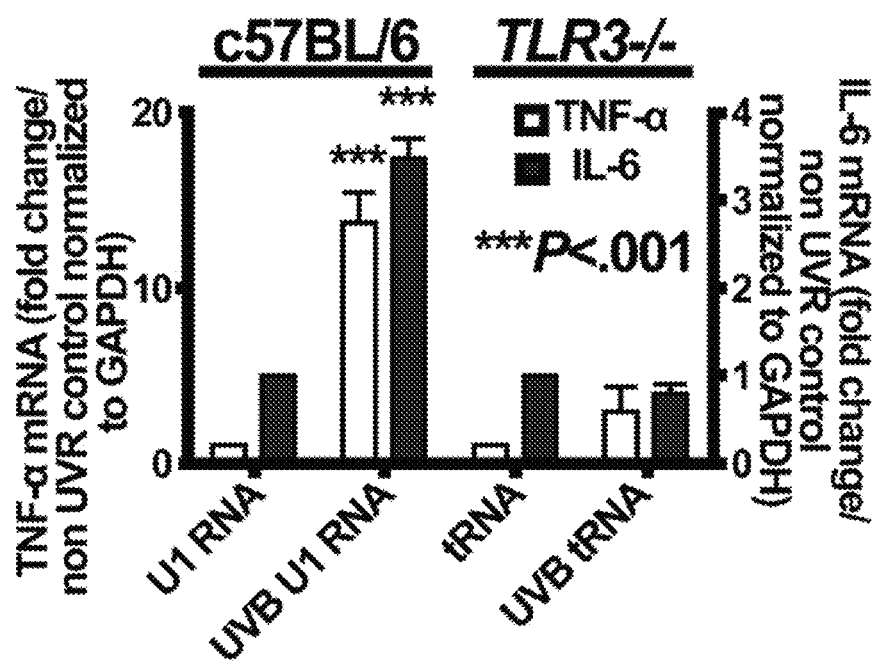
Figure 10:
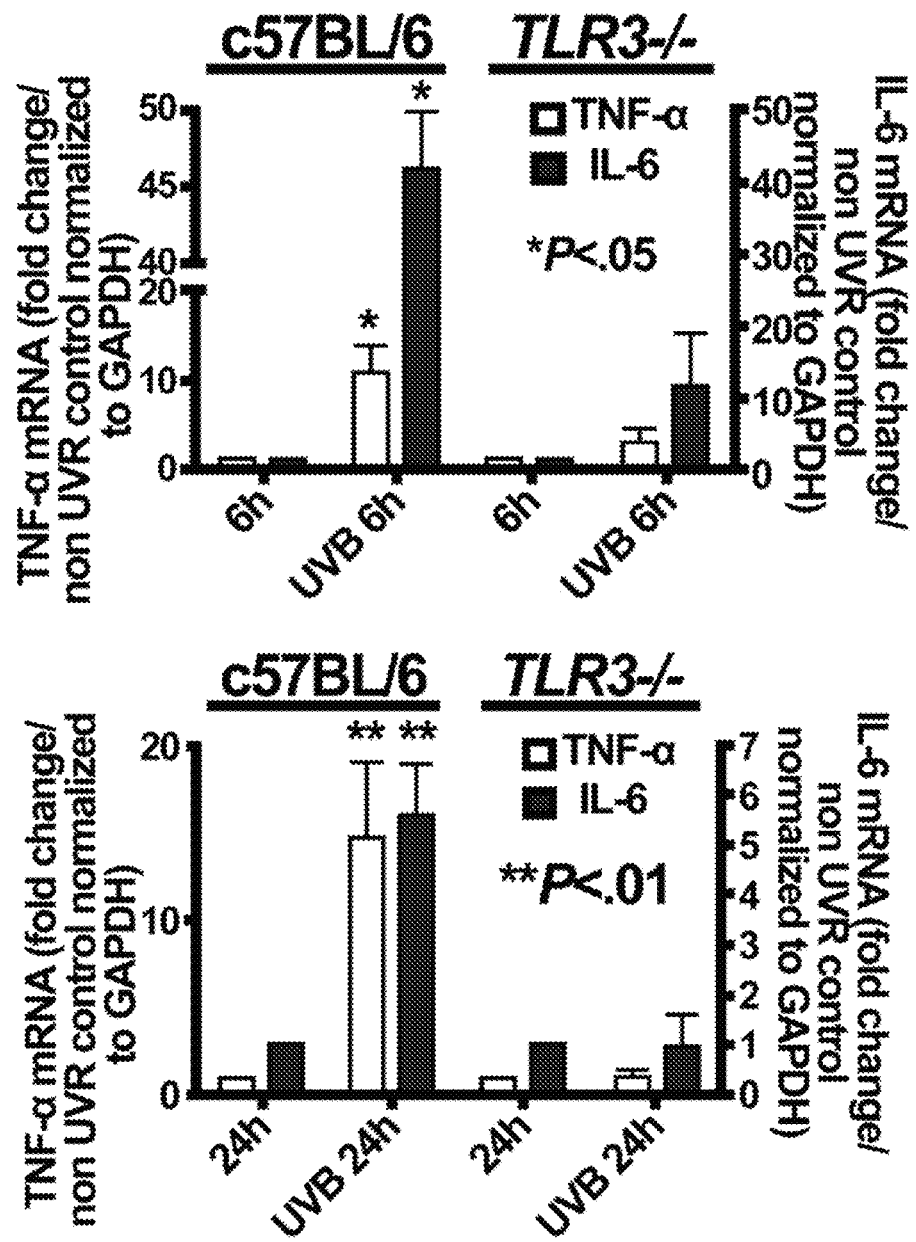
FIG. 10 shows that TLF3$^{-/-}$ mice are unable to increase TNF-α or IL-6 mRNA abundance following UVB irradiation.

As the cytokine response to whole preparations of UVB exposed cells was shown earlier to be dependent on TLR3, the response of the canonical pattern recognition signaling system of TLR3 to U1 RNA was examined. Steady-state TLR3 mRNA expression was significantly induced in cells after exposure to U1 RNA damaged by UVB (FIG. 3a) and, similar to the response seen in FIG. 1 after exposure to whole UVR-treated keratinocyte extracts, TLR3 siRNA attenuated the ability of U1 RNA to induce TNF-α (FIG. 3b, c and FIG. 9) and IL-6 (FIG. 9). Since UV exposure has previously been shown to activate nuclear factor-kappa B (NF-κB) signaling, and double-stranded RNA can induce activation of NF-κB via TLR3, the influence of UVB U1 RNA on NF-κB nuclear localization was examined. UVB U1 RNA induced the translocation of RelA/p65 to the nucleus at 4 hrs as assayed by Western blot of nuclear extract or direct immunofluorescence (FIG. 3e, d).

Figure 4:
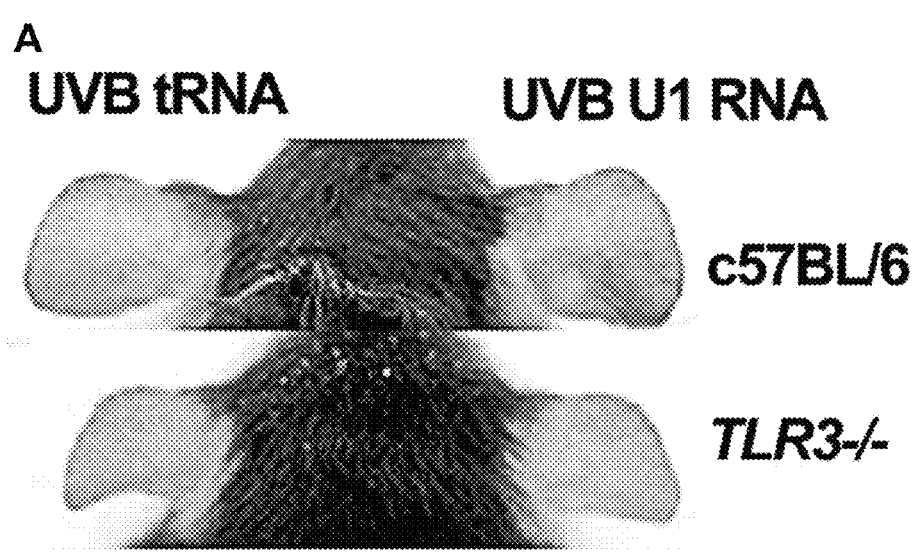
FIG. 4A-F shows RNA recognition by TLR3 is necessary for skin cytokine response to UV damage. (A) Mouse ears 24 hrs following ear injections of UVB tRNA or UVB U1 RNA (n=4). (B) Micrometer measurements of ear thickness 24 hrs following ear injections of UVB U1 RNA or UVB tRNA ($*p<0.001$). qRT-PCR analysis of TNF-α (C) ($*p<0.001$) and IL-6 (D) ($*p<0.001$) 24 hrs following ear injections of UVB tRNA or UVB U1 RNA. c57BL/6 and TLR3$^{-/-}$ were exposed to 5 kJ/m2 UVB and back skin punch biopsies were performed 6 and 24 hrs. qRT-PCR analysis of TNF-α (E) ($p<0.01$, $*p<0.05$) and IL-6 (F) ($**p<0.01$).
Figure 4:
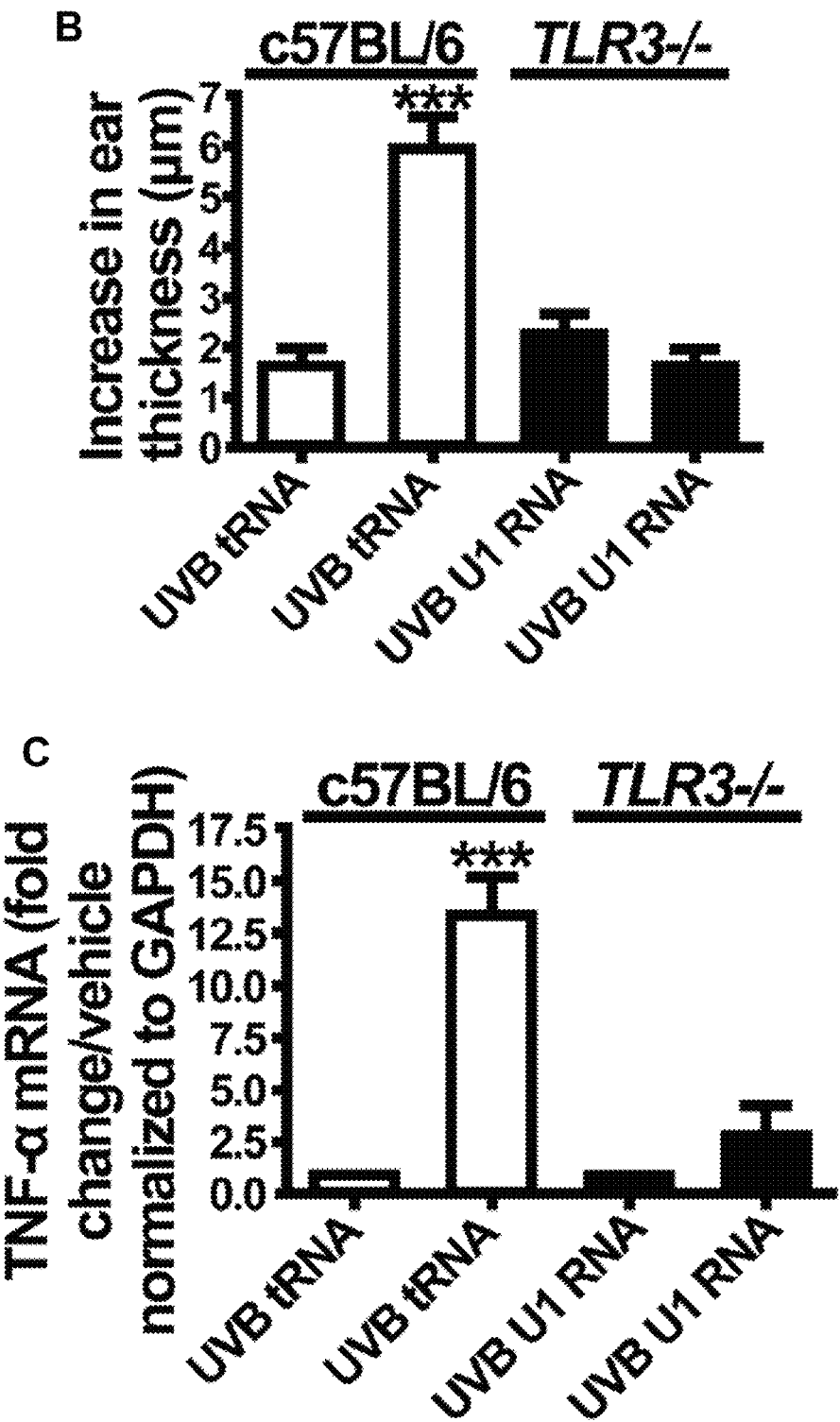
Figure 4:
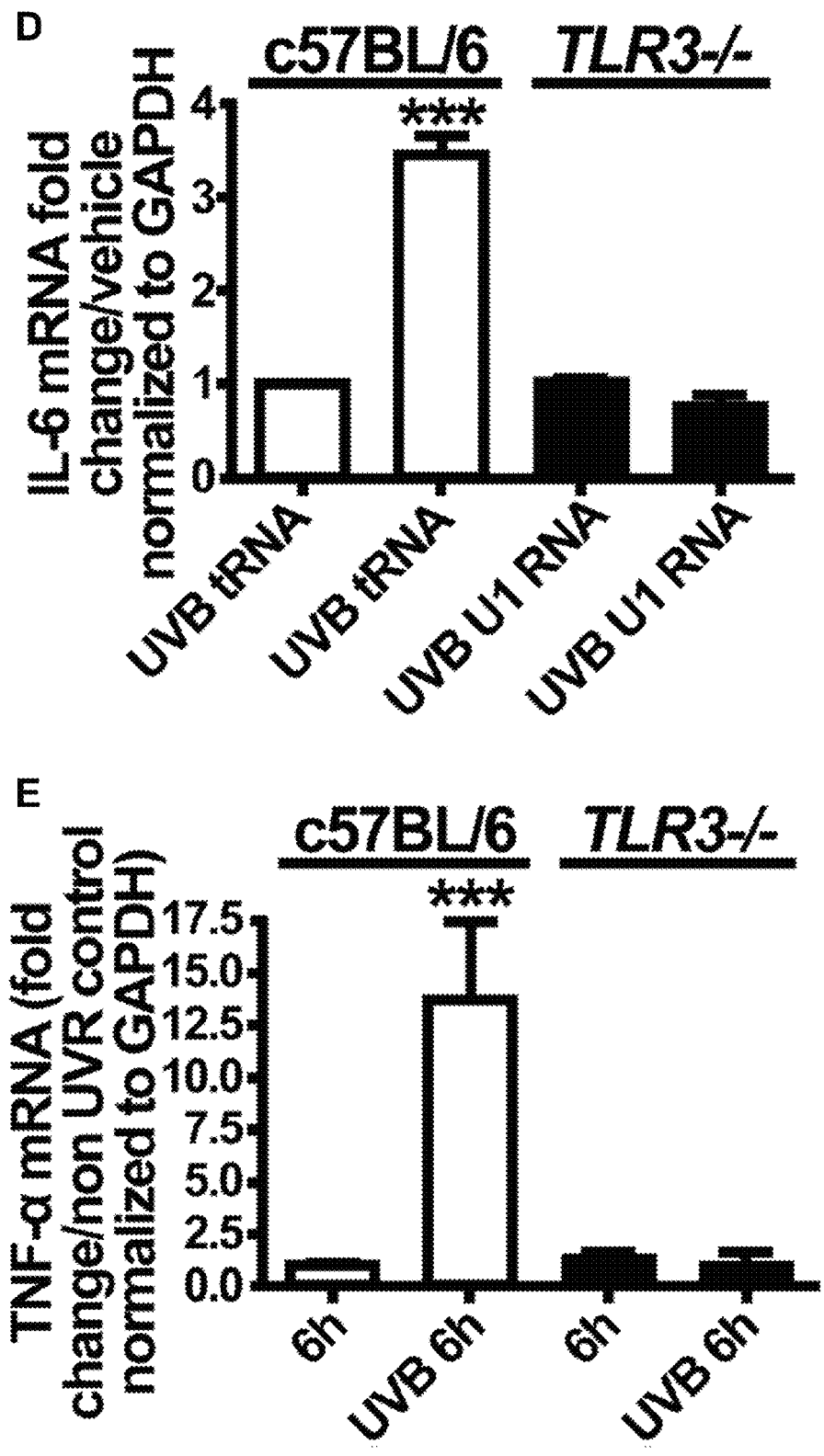
Figure 4:
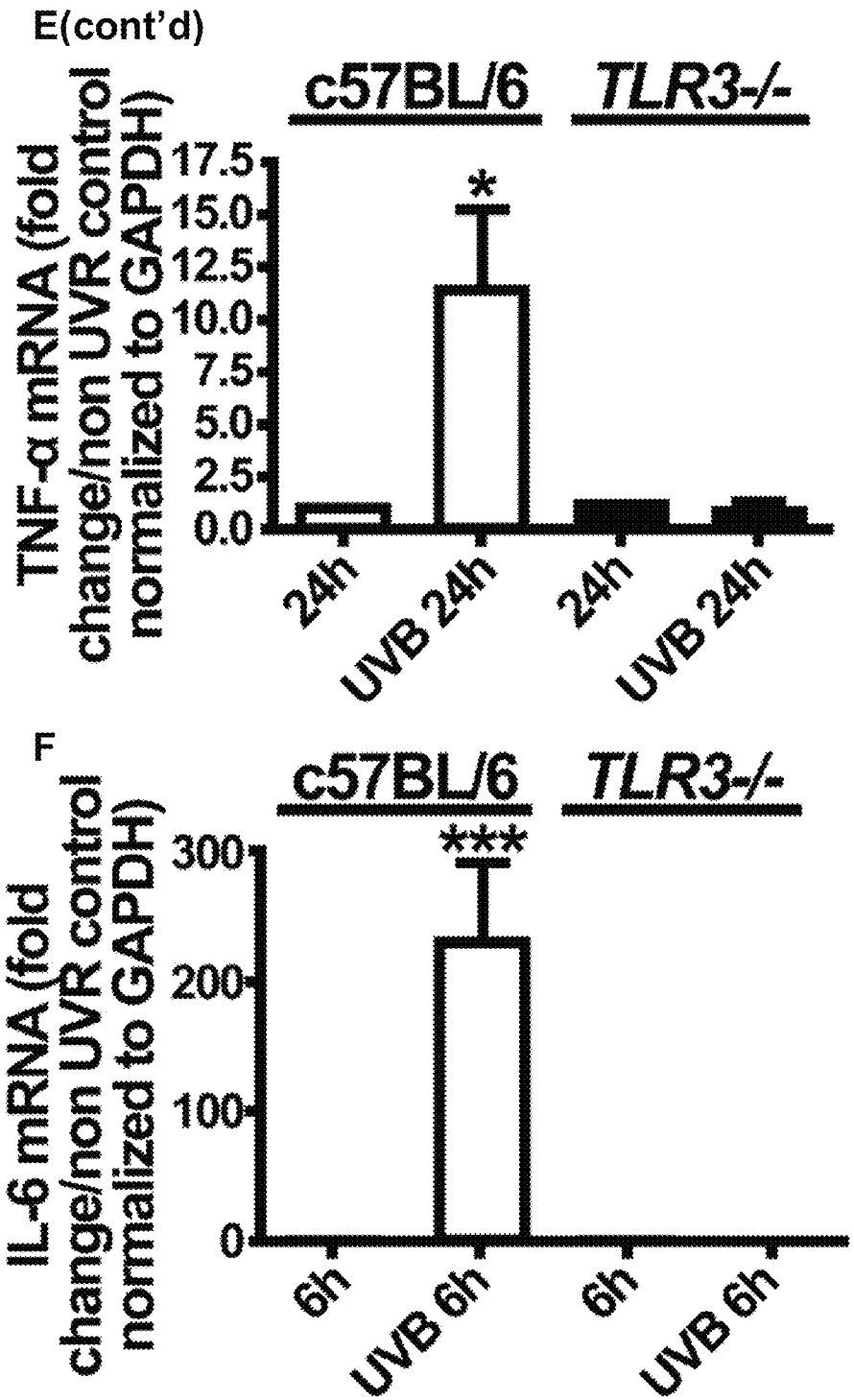
Figure 4:
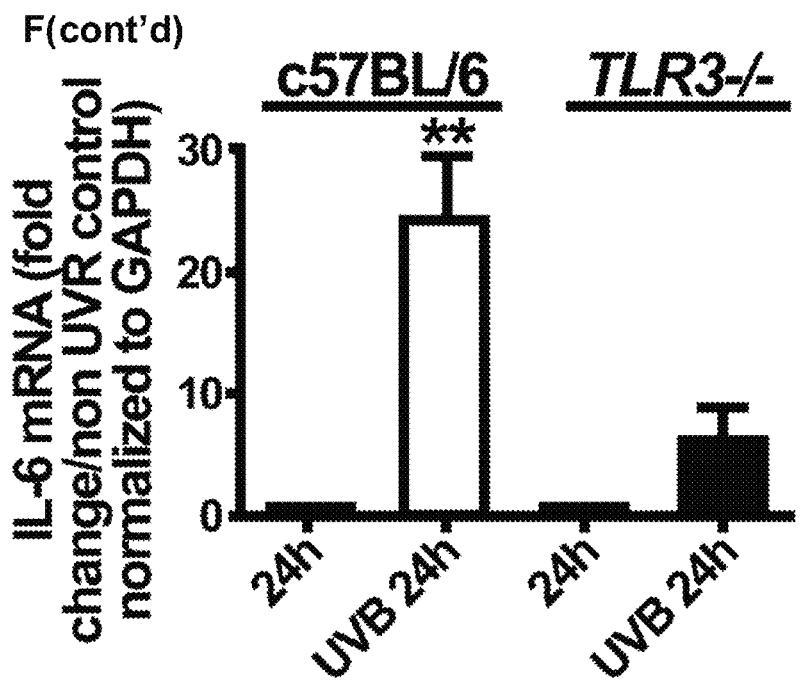

To establish that U1 RNA could act as transferrable signal of UV injury in vivo, the effects of UVB treated U1 RNA in mouse models similar to those used in FIG. 1 was examined. UVB U1 RNA, or UVB treated tRNA used as a control, was injected intradermally (1 μg) into c57BL/6 and TLR3$^{-/-}$ mouse ears. In c57BL/6 mice, UVB U1 RNA induced erythema (FIG. 4a) and increased ear thickness (FIG. 4b) while UVB tRNA failed to induce a visible cutaneous phenotype or increase in ear thickness (FIG. 4a, b). The increased inflammation observed after injection of UVB U1 RNA corresponded with an increase in the expression of both TNF-α (FIG. 4c) and IL-6 (FIG. 4d) mRNA, and was dependent on both TLR3 and TRIF.

The direct inflammatory cytokine response to exposure of UVB in vivo was dependent on the function of TLR3, therefore supporting the position that endogenous dsRNA mediates this effect in a physiologically relevant manner. Hair was removed, and mice were exposed to UVB followed by biopsy of the back skin 6 and 24 hrs after irradiation. As predicted, lack of TLR3 significantly abrogated the expression of both TNF-α and IL-6 mRNA in the skin (FIG. 4e, f).

These observations provide a framework to understand the inflammatory response experienced by most humans, but previously unexplained. In the absence of an adequate protective shield, humans are susceptible to severe short and long-term damage due to excessive solar exposure. The capacity to sense this injury is critical to modifying behavior, and if tissue damage occurs, inflammation is important for both resisting infection and repairing damage. Previous investigations of cutaneous responses to UV exposure have identified mast cell degranulation, IL-1 release and NF-κb activation as important cellular responses to UV exposure, but a molecular mechanism to explain the inflammatory response had yet to be defined. The disclosure demonstrates that alterations to non-coding RNA, and recognition of this injury by a pattern recognition receptor classically thought to respond only to viral RNA, is a fundamental step in this process.

Support for the concept that endogenous nucleic acids can serve as ligands for TLRs has been seen in several experimental models including the inflammatory response to necrosis of the gut and skin, and autoimmune phenomena. However, the role of RNA damage in the normal sunburn response was not previously suspected. The unique application of RNA-Seq used here identified changes in several other non-coding RNAs that may also contribute to the UV inflammatory response, but isolation and analysis of U1 RNA confirmed species of RNA as at least one of several with a potential role in the system. Other cellular products of UV exposure have previously been identified including, urocanic acid, telomeric nucleotides, and 6-formylindolo(3,2-b) carbazole. These molecules, as well as the release of inflammatory mediators such as IL-1 from keratinocytes, contribute to the sunburn and subsequent tanning response. However, these molecules do not contribute in a major way to the immediate cytokine response since the data show a greatly attenuated inflammatory response to UV in TLR3 knockdown cells and TLR3$^{-/-}$ mice. This establishes TLR3 as an essential sensor for UV stimulation of cytokine production, and suggests that alternate RNA sensors such as PKR, RIG-1, MDA, and TLR8 have a negligible role. Furthermore, since previously identified UV products do not act through TLR3, and in the case of telomeric nucleotides were not active when directly tested in the assays, these molecules are not the stimulus of increased TNF-α and IL-6 production, or the transferrable UV inflammatory response observed here. Therefore, the results demonstrate that damage to RNA is a critical trigger of the UV inflammatory cytokine response.

U1 RNA has been considered a potential element in the pathogenesis of tissue inflammation in systemic lupus erythematosus (SLE), a highly photosensitive disorder. It is attractive to speculate that the photosensitivity manifested by these patients is a reflection of an enhanced normal response to U1 RNA damage either due to increased accessibility to U1 RNA or altered recognition. Chloroquine, an inhibitor of endosomal TLRs that has demonstrated efficacy in the treatment of SLE, has been shown to protect against UV-induced erythema, but not UV-induced pigmentation when applied topically to healthy skin. With this new information regarding how UVB mediates the induction of inflammatory cytokines the disclosure provides a mechanism for the origin of UV-induced inflammation that may influence the understanding and therapy of a wide-range of photosensitive phenomena.

Cell culture. Normal human epidermal keratinocytes (NHEKs) were grown in serum-free EpiLife cell culture media (Cascade Biologics, Portland, Oreg.) containing 0.06 mM Ca$^{2+}$ and 1× EpiLife Defined Growth Supplement at 37° C. under standard tissue culture conditions. The cultures were maintained for up to four passages in this media with the addition of 50 U/mL penicillin and 50 μg/mL of streptomycin. Cells were treated at 70-80% confluence. Human PBMC were prepared by Ficoll density gradient separation.

Mice. TLR3-deficient and TRIF-deficient mice in C57BL/6 background, as well as wild-type controls, were house at the University Research Center at the University of California, San Diego (UCSD). All animal experiments were approved by the UCSD Institutional Animal Care and Use Committee. Mice were administered intradermal ear injections of UVR keratinocytes ($1.2 \times 10^5$) or UVB U1 RNA (1 μg) (described below). Ear thickness was measured using a micrometer. Six mm punch biopsies were performed following CO$_2$ euthanasia to harvest tissue for histological, mRNA and protein analyses.

UVB exposure. NHEK were irradiated by UVB at 15 mJ/cm$^2$ as previously described[8] using a single FS-40 bulb. Dosimetry was determined using a digital ultraviolet radiometer by Solartech Inc. UVR-cells were used fresh and 600,000 necrotic cells were added to 200,000 NHEKs grown to 80% confluence or 200,000 PBMCs. Sonicated-non-irradiated NHEKs used identically were used as a control. TNF-α and IL-6 were measured in the culture media and mRNA was measured from treated cells 24 hours after culture in presence of UVB treated cells. Hair was finger plucked from mice and 24 hrs later mice exposed to UVB (5 kJ/m$^2$). Skin was biopsied 6 and 24 hours after irradiation.

RNA-Seq. Sequencing libraries were prepared using double-stranded cDNA produced using NuGEN RNASeq Ovation kits and 100 ng of total RNA starting material for each sample following the manufacturer's protocols. 100 ng of double stranded cDNA was digested with 50 units S1 nuclease (Promega) for 30 min at 37° C. in 50 mM sodium acetate (pH 4.5), 280 mM NaCl, and 4.5 mM $ZnSO_4$. The cDNA library was purified using DNA Clean&Concentrator™-5 Kit (Zymo Research Corp). DNA ends were repaired using 15 units T4 DNA polymerase (Enzymatics), 5 units Klenow Large Fragment (Enzymatics), and 50 units T4 polynucleotide kinase (Enzymatics) at 20 C for 30 minutes in 50 mM Tris-HCl (pH 7.5), 10 mM $MgCl_2$, 1 mM ATP, 10 mM dithiothreitol, and 400 µM dNTP mixture. DNA products were purified again using DNA Clean&Concentrator™-5 Kit. Next, DNA ends were A-tailed with 15 units Klenow (3'→5' exo-)(Enzymatics) at 37C for 30 min. in 10 mM Tris-HCl (pH 7.9), 50 mM NaCl, 10 mM $MgCl_2$, 1 mM dithiothreitol, and 0.2 mM dATP. DNA products were again purified using the DNA Clean&Concentrator™-5 Kit. Next, Illumina Paired End-adapter oligonucleotides, at 2 µM concentration, were ligated to the A-tailed cDNA ends with 3,000 units T4 DNA ligase (Enzymatics) at 20° C. for 15 minutes in 66 mM Tris-HCl (pH 7.6), 10 mM $MgCl_2$, 1 mM dithiothreitol, 1 mM ATP, 1 mM PEG. DNA products were purified using DNA Clean&Concentrator™-5 Kit. The DNA library products were then separated on a 2% NuSieve GTG® agarose gel (Lonza) and products corresponding to a size of approximately 200-300 bases were excised from the gel and isolated using Zymoclean™Gel DNA Recovery Kit (Zymo Research). The excised DNA material was PCR amplified with 1 unit of Phusion™ Polymerase (Finnzymes) in standard 1X Phusion™ HF buffer with 0.2 mM dNTPs and 0.6 µM PCR primers PE 1.0 and PE 2.0 (Illumina) for 15 cycles. The amplified DNA products were further purified on 2% NuSieve GTG® agarose gel (Lonza), excised, and isolated again using Zymoclean™Gel DNA recovery kit. The purified DNA library was quantitated using the Qubit quantitation platform (Invitrogen) and sized using the 2100 Bioanalyzer (Agilent). DNA products were then denatured in 0.1N NaOH and diluted to a final concentration of 10 µM before being loaded onto the Illumina paired-end flow-cell for massively parallel sequencing by synthesis on the Illumina GAIIx.

RNA-Seq analysis. The raw data output from the Illumina Genome Analyzer was in fastq format, representing the sequence and quality scores for each read. The reads were filtered based on quality using FASTX-Toolkit, selecting for reads with a minimum PHRED64 quality of 20 in 90% of the bases of the read. The reads passing the filter were aligned using Bowtie to three in-house generated indexes, based on downloaded sequences for HG19, miRBase Release 15, and snoRNABase. The output SAM file was filtered for alignment using Samtools, sorted, and converted to a BAM file. BEDTools was used to intersect the BAM alignment data to the annotated genomic intervals corresponding to the Bowtie indexes, producing hit counts for each region.

RNA production. In vitro transcribed U1 RNA was kindly donated from Dr. Eric L. Greidinger (University of Miami and the Miami VA Medical Center; Miami, Fla.) and was synthesized as previously described. When indicated, U1 RNA or transfer RNA Sigma Aldrich (St. Louis, Mo.) (tRNA) was exposed to UVB (15 $mJ/cm^2$).

RNA size analysis. U1 RNA exposed to UVR (15 $mJ/cm^2$), or non-irradiated U1 RNA, was biotinylated using the Ambion psoralin-biotin kit according to the manufacturer's instructions, and separated by size using Illustra MicroSpin® S-200 HR columns (GE Healthcare). Fractions were obtained by eluting the columns with 50 µL of water three times. Fractions were dot-blotted on a nylon membrane (Pall Corporation), blocked with Odyssey® Infrared Imaging System Blocking Buffer (LI-COR Biosciences, Lincoln, Nebr.) with 1% SDS, and probed with streptavidin IRDye® 800CW. Blot was washed three times and visualized on the Odyssey and proportion of U1 RNA in each fraction determined by densitometry. For bioanalyzer evaluation, U1 RNA was quantified using the NanoDrop ND-1000. Sample size and qualitity was analyzed using the Agilent 2100 Bioanalyzer Small RNA Assay Kit (Santa Clara, Calif.) according to the manufacturer's instructions.

TLR3 siRNA. NHEKs were transfected with 25 nM of four pairs of siRNA oligonucleotides (Dharmacon; SMART Pool) targeted to TLR3 siRNA using Dharmafect (Thermo Fisher Scientific) transfection reagent. Non-targeted siRNA (Dharmacon) was used as a control. Cells were incubated for 24 hrs and the transfection was repeated. Twenty-four hours after the last transfection, cells were treated with UVR NHEKs or U1 RNA.

Real-time quantitative RT-PCR. Total RNA was extracted by using Trizol Reagent (Invitrogen, Carlsbad, Calif.). One microgram of total RNA was used for cDNA synthesis by the iSCRIPT cDNA Synthesis Kit (Bio-Rad, Hercules, Calif.) according to the manufacturer's instructions. Real-time RT-PCR was conducted in an ABI PRISM 7000 sequence detector (Applied Biosystems, Carlsbad, Calif.). The primers and probes used for real-time RT-PCR were purchased from Applied Biosystems. RNA analysis was performed using the TaqMan Master Mix reagents kit (Applied Biosystems). The quantification of gene expression was determined by the comparative $\Delta\Delta C_T$ method. The target gene expression in the test samples was normalized to the endogenous reference Glyceraldehyde 3-phosphate dehydrogenase (GAPDH) level and was reported as the fold difference relative to the GAPDH gene expression. All the assays were performed in triplicate and repeated at least 3 times.

Western blotting. Nuclear lysates were separated from cytoplasmic lysates using a PARIST™ Kit (Ambion, Austin, Tex.). Ten percent gels were run and transferred onto PVDF transfer membranes (Millipore). Membranes were blocked with the Odyssey® Infrared Imaging System Blocking Buffer (LI-COR Biosciences, Lincoln, Nebr.) then incubated with an anti-RelA/p65 (Santa Cruz Biotechnology, Santa Cruz, Calif.), or anti-lamin B1 (Abcam, Cambridge, Mass.) primary antibodies in 5% blocking buffer for 2 hrs at room temperature. Membranes were washed and incubated with goat anti-rabbit IRDye® 680 or goat anti-mouse IRDye® 800CW secondary antibodies (LI-COR Biosciences, Lincoln Nebr.) for 30 min at room temperature. Membranes were washed and fluorescence was detected using the Odyssey® Infrared Imaging System (LI-COR Biosciences). Western blotting for each protein was repeated at least 3 times.

Enzyme-linked immunosorbent assay (ELISA). Supernatants were assayed by the TNF-α or IL-6 ELISAs from BD Biosciences (San Diego, Calif.) according to the manufacturer's instructions. These assays were performed in triplicate and repeated 3 times.

Confocal microscopy. NHEKs were treated with biotinylated UVB U1 RNA for 8 hr. Cells were fixed and stained using an intracellular Toll-like receptor staining kit from Imgenex (San Diego, Calif.). Cells were incubated with a mouse IgG TLR3 Alexa Fluor 647 antibody (Imgenex) or a mouse IgG isotype control and an Avidin Alexa Fluor 488 conjugate for 1 hr. Cells were photographed with a confocal microscope (Zeiss LSM 5 Pascal).

Fluorescence microscopy. NHEKs were grown on chamber slides and treated as described in the Results. Cells were fixed in 2% formaldehyde for 15 min, washed with 1× phosphate buffer saline (PBS), blocked in 3% bovine serum albumin (BSA) for 30 min and stained with a rabbit anti-p65 antibody (Santa Cruz Biotechnology (1:200) or rabbit IgG for 2 hrs at room temperature. Cells were then washed with 1× PBS stained with Alexa Fluor® 568 goat anti-rabbit IgG (1:1000) for 1 hr at room temperature. Cells were washed with 1× PBS, mounted in ProLong Anti-Fade reagent containing 4',6-diamidino-2-phenylindole (Molecular Probes, Eugene, Oreg.) and evaluated with an Olympus BX41 microscope (Olympus, Mellville, N.Y.) at original magnification of 400×.

Statistical analysis. To determine the significances between groups, comparisons were made by using two-tailed t tests. Analyses of multiple groups were done by One-way or Two-way ANOVA with Bonferroni post-test of GraphPad Prism Version 4. For all statistical tests, P values <0.05 was accepted for statistical significance.

A number of embodiments of the invention have been described. Nevertheless, it will be understood that various modifications may be made without departing from the spirit and scope of the invention. Accordingly, other embodiments are within the scope of the following claims.

What is claimed is:

1. A composition comprising a nucleotide sequence selected from the group consisting of:

(i) loop "a" of U1 snRNA consisting of GGGAGAACCAUGAUCACGAAGGUGGUUUUCCC (SEQ ID NO:2);

(ii) loop "b" of U1 snRNA consisting of GGGCGAGGCUUAUCCAUUGCACUCCGGAUGUGCUGACCCC (SEQ ID NO:3);

(iii) a fragment of a loop "c" of U1 snRNA consisting of 10-26 nucleotides of CGAUUUCCCCAAAUGUGGGAAACUCG (SEQ ID NO:4);

(iv) any of the foregoing sequences wherein U is T;

(v) complements of any of the foregoing sequences;

(vi) any of the foregoing sequences comprising a non-natural nucleotide; and (vii) an oligonucleotide having 99% identity with any of the foregoing sequences wherein the oligonucleotide can stimulate IL-6 and/or TNF α production in a mammalian cell, wherein the nucleotide sequence is chemically linked to a charge neutralizing agent and wherein the composition comprises a pharmaceutically acceptable carrier.

2. A method of inducing inflammation comprising contacting a tissue with a composition of claim 1, wherein the composition induces TNF-alpha and/or IL-6 production.

3. A method of treating an infection in a subject comprising contacting a tissue with a composition of claim 1, wherein the composition induces TNF-alpha and/or IL-6 production.

4. The method of claim 3, wherein the infection is a skin infection.

5. A method of treating a skin wound comprising contacting a tissue with a composition of claim 1, wherein the composition induces TNF-alpha and/or IL-6 production.

* * * * *